United States Patent
Hosoya

(10) Patent No.: US 8,951,483 B2
(45) Date of Patent: Feb. 10, 2015

(54) EXAMINATION ELEMENT AND EXAMINATION CONTAINER

(75) Inventor: Kunio Hosoya, Atsugi (JP)

(73) Assignee: Semiconductor Energy Laboratory Co., Ltd., Atsugi-shi, Kanagawa-ken (JP)

(*) Notice: Subject to any disclaimer, the term of this patent is extended or adjusted under 35 U.S.C. 154(b) by 1225 days.

(21) Appl. No.: 11/898,406

(22) Filed: Sep. 12, 2007

(65) Prior Publication Data

US 2008/0060422 A1    Mar. 13, 2008

(30) Foreign Application Priority Data

Sep. 13, 2006  (JP) .................................. 2006-247978

(51) Int. Cl.
| | |
|---|---|
| G01N 33/48 | (2006.01) |
| G01N 33/483 | (2006.01) |
| G01N 33/487 | (2006.01) |
| G01N 33/497 | (2006.01) |
| G01N 33/50 | (2006.01) |
| G01N 33/52 | (2006.01) |
| G01N 21/78 | (2006.01) |
| A61B 10/00 | (2006.01) |
| G01N 33/493 | (2006.01) |

(52) U.S. Cl.
CPC .............. *G01N 21/78* (2013.01); *A61B 10/007* (2013.01); *G01N 33/493* (2013.01)
USPC ............. 422/403; 422/50; 422/400; 422/401; 422/402; 422/68.1; 422/82.05

(58) Field of Classification Search
USPC ................. 422/50, 55–58, 68.1, 82.05–82.09
See application file for complete search history.

(56) References Cited

U.S. PATENT DOCUMENTS

| | | | | |
|---|---|---|---|---|
| 3,629,873 | A | * | 12/1971 | Long ................................. 4/220 |
| 5,184,359 | A | | 2/1993 | Tsukamura et al. |
| 5,217,443 | A | | 6/1993 | Oxley |
| 5,558,638 | A | | 9/1996 | Evers et al. |
| 5,882,931 | A | | 3/1999 | Petersen |
| 6,117,643 | A | * | 9/2000 | Simpson et al. ............... 435/7.1 |
| 6,217,744 | B1 | | 4/2001 | Crosby |
| 6,375,897 | B1 | | 4/2002 | Bachand |

(Continued)

FOREIGN PATENT DOCUMENTS

| | | |
|---|---|---|
| DE | 102004048864 | 4/2006 |
| EP | 1564839 A | 8/2005 |

(Continued)

OTHER PUBLICATIONS

Search Report (Application No. 07017671.4) Dated Jan. 18, 2010.

*Primary Examiner* — In Suk Bullock
*Assistant Examiner* — Robert Eom
(74) *Attorney, Agent, or Firm* — Eric J. Robinson; Robinson Intellectual Property Law Office, P.C.

(57) ABSTRACT

The present invention relates to an examination element that includes an antenna; a hygroscopic portion that absorbs a specimen; a reagent portion that, reacts with the specimen; and a chip including a semiconductor device capable of wireless communication and a photo sensor that detects a change in a color of the reagent portion. A change in the reagent portion is detected by the photo sensor, the detected data is stored in the semiconductor device capable of wireless communication, and the data is transmitted to an external database.

16 Claims, 20 Drawing Sheets

(56) References Cited

U.S. PATENT DOCUMENTS

| | | | |
|---|---|---|---|
| 6,673,596 | B1 | 1/2004 | Sayler et al. |
| 6,698,583 | B2 | 3/2004 | Itoh |
| 6,905,834 | B1 | 6/2005 | Simpson et al. |
| 7,090,992 | B2 | 8/2006 | Simpson et al. |
| 7,208,286 | B2 | 4/2007 | Simpson et al. |
| 7,355,270 | B2 | 4/2008 | Hasebe et al. |
| 7,371,538 | B2 | 5/2008 | Simpson et al. |
| 7,545,272 | B2 | 6/2009 | Goodnow et al. |
| 7,988,917 | B2 | 8/2011 | Roesicke et al. |
| 2003/0099572 | A1 | 5/2003 | Ng et al. |
| 2003/0114735 | A1* | 6/2003 | Silver et al. .............. 600/300 |
| 2005/0022581 | A1* | 2/2005 | Sunshine .................. 73/31.05 |
| 2005/0104149 | A1 | 5/2005 | Bauer et al. |
| 2006/0226985 | A1 | 10/2006 | Goodnow et al. |
| 2007/0237678 | A1 | 10/2007 | Roesicke et al. |
| 2007/0270672 | A1 | 11/2007 | Hayter |
| 2008/0114228 | A1 | 5/2008 | McCluskey et al. |

FOREIGN PATENT DOCUMENTS

| | | |
|---|---|---|
| JP | 05-018966 | 1/1993 |
| JP | 10-197526 A | 7/1998 |
| JP | 2001-524667 | 12/2001 |
| JP | 2003-532054 | 10/2003 |
| JP | 2004-139345 A | 5/2004 |
| JP | 2005-228785 A | 8/2005 |
| JP | 2006-052951 | 2/2006 |
| WO | WO-99/27351 | 6/1999 |
| WO | WO-01/61347 | 8/2001 |
| WO | WO-02/23168 | 3/2002 |
| WO | WO-2006/009404 | 1/2006 |
| WO | WO-2006/026741 | 3/2006 |
| WO | WO 2006/026741 A1 * | 3/2006 |
| WO | WO-2006/026748 | 3/2006 |
| WO | WO-2006/040083 | 4/2006 |
| WO | WO-2006/086423 | 8/2006 |

* cited by examiner

EXAMINATION ELEMENT AND EXAMINATION CONTAINER

BACKGROUND OF THE INVENTION

1. Field of the Invention

The present invention relates to a urinalysis system including a semiconductor device capable of wireless communication, a photo sensor, or the like, and a urinalysis method using the urinalysis system.

2. Description of the Related Art

A urinalysis mainly tests for kidney diseases, but also tests for various other diseases. Conventionally, a method of preparing a paper cup for urinalysis and dipping a test paper into collected urine to manually obtain a reaction appearing on the test paper is employed for urinalysis.

With urinalysis test paper, the following can be tested: protein in urine, urine sugar, ketone body, bilirubin, urobilinogen, occult blood, nitrite, pH, specific gravity of urine and the like. In recent years, with the development of information description, advanced networks are being built in the medical workplace. However, there is no technique to electronically connect such test results obtained manually. That is, information of the test results needs to be input to an information terminal by hand, which has hindered improvement in quickness and efficiency.

As an automation apparatus, an automatic urinalysis apparatus is known, which has a sensor unit that is provided inside a urinalysis tool including a waterproof container provided with an examination hole and a reagent portion, which seals the examination hole. The sensor unit includes a light receiving element and a light emitting element for optically detecting the degree of coloration of the reagent portion (see Patent Document 1: Japanese Published Patent Application No. H 5-18966).

However, with a method of soaking the urinalysis tool in a container containing a specimen for a certain amount of time and measuring the degree of coloration of the reagent portion each time, it takes a long time to process many specimens. Also, for every specimen, the urinalysis tool to which the reagent portion is attached, and the sensor unit need to be taken apart to replace the urinalysis tool with a new one.

SUMMARY OF THE INVENTION

Consequently, an object of the present invention is to automate analysis of a specimen, and to improve quickness and efficiency in medical practice.

In addition, the present invention is not limited to medical practice, and another object is to improve quickness and efficiency of testing means for testing liquid, and a testing method.

The present invention relates to an examination element or an examination container that can be used favorably in examining a specimen, and the main point is that it is provided with functions of detecting a change in a reagent portion by a sensor and outputting the sensor output by wireless communication to a computer.

The present invention relates to an examination element that includes an antenna; a hygroscopic portion that absorbs a specimen; a reagent portion that is provided in contact with the hygroscopic portion and reacts with the specimen; a chip including a semiconductor device capable of wireless communication and a photo sensor that detects a change in a color of the reagent portion; and a light transmitting protective film that covers the antenna and the chip. A change in the reagent portion is detected by the photo sensor, the detected data is stored in the semiconductor device capable of wireless communication, and the data is transmitted to an external database.

Also, the present invention relates to an examination element that includes a hygroscopic portion that absorbs a specimen; a reagent portion that is provided in contact with the hygroscopic portion and reacts with the specimen; a photo sensor that detects a change in a color of the reagent portion; a signal processing circuit that reads an output from the photo sensor; and a communication circuit that outputs an output of the signal processing circuit to an external device.

Further, the present invention relates to an examination container that includes a container and an examination element provided in the container. The examination element includes an antenna, a chip including a photo sensor and a semiconductor capable of wireless communication, a light transmitting protective film covering the antenna and the chip, a reagent portion, and a hygroscopic portion. Also, a change of the reagent portion is detected by the photo sensor, the detected data is stored in the semiconductor device capable of wireless communication, and the data is transmitted to an external database.

Furthermore, the present invention relates to an examination container that includes an examination element in a vicinity of a bottom surface of a cylindrical body with a bottom that stores a specimen, and the examination element includes, for example, the following: a hygroscopic portion that absorbs the specimen; a reagent portion that is provided in contact with the hygroscopic portion and reacts with the specimen; a photo sensor that detects a change in a color of the reagent portion; a signal processing circuit that reads an output of the photo sensor; and a communication circuit that outputs an output of the signal processing circuit to an external device.

Still further, the present invention relates to an examination container that includes an examination element in a vicinity of a bottom surface of a cylindrical body with a bottom that stores a specimen, and the examination element includes the following: a hygroscopic portion that absorbs the specimen; a reagent portion that is provided in contact with the hygroscopic portion and reacts with the specimen; a photo sensor that detects a change in a color of the reagent portion; a signal processing circuit that reads an output of the photo sensor; and a communication circuit that outputs an output of the signal processing circuit to an external device. Also, an antenna formed on a bottom surface or a side surface of the cylindrical body and the examination element are connected.

In the present invention, the photo sensor includes a photo diode and an amplifier circuit that amplifies an output current of the photo diode.

In the present invention, the semiconductor device capable of wireless communication includes a memory circuit, and the memory circuit stores the detected data and the stored data is transmitted to the external database.

In the present invention, a battery for supplying power is provided.

Also, in the present invention, the battery is an RF battery.

By the present invention, it is possible to speed up a medical examination as well as to improve efficiency of medical service.

DETAILED DESCRIPTION OF THE INVENTION

Embodiment Mode

Figure 1A:
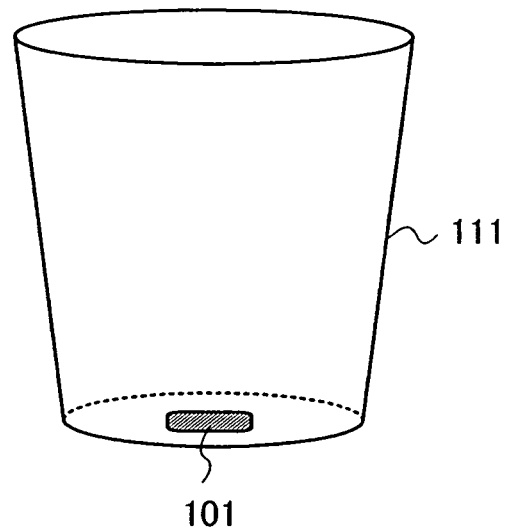
FIGS. 1A and 1B show outlines of the present invention.

An embodiment mode of the present invention will hereinafter be described. However, the present invention can be carried out in many different modes, and it is easily understood by those skilled in the art that modes and details herein disclosed can be modified in various ways without departing from the spirit and the scope of the present invention. Therefore, the present invention should not be interpreted as being limited to the description of the embodiment mode to be given below.

Note that in all drawings for describing the embodiment mode, the same reference numerals are used for the same portions or the portions having similar functions, and repeated description thereof is omitted.

Note that a semiconductor device in this specification refers to devices in general that can function by utilizing a semiconductor characteristic.

This embodiment will be described with reference to FIGS. 1A to 20.

An examination element 101 for examination (see FIG. 1A) is attached to an inside of a container 111 for urinalysis, for example, a cylindrical object with a bottom, specifically, a paper cup. The examination element 101 includes a substrate 102 made of a resin such as polyimide, a chip 105 provided over the substrate 102, an antenna 103 made of a conductor such as copper, a light emitting element (light emitting diode (LED)) 104 provided over the substrate, a light transmitting protective film 107 provided over the chip 105, a reagent portion 108 provided over the protective film 107, and a hygroscopic portion 109 provided over the reagent portion 108 (see FIG. 1B). Note that although in FIG. 1B, a light transmitting passivation film 106 for protecting the chip 105 is provided, the passivation film 106 does not have to be formed since the protective film 107 is provided.

Note that a hygroscopic material used for the hygroscopic portion 109 may be any material that absorbs a specimen, in this embodiment mode, a liquid. A resin or a porous body can be given as examples.

An examination element for examination is attached to an inside (preferably, the bottom) of a paper cup for urinalysis that is used conventionally. A test paper that is provided over a top surface of the examination element reacts to urine (specimen) that is collected in the paper cup, the reaction is read by a photo sensor mounted to the examination element, and data of a test result is sent to a semiconductor device capable of wireless communication. Then, the semiconductor device capable of wireless communication, which is mounted to the examination element, digitizes information and temporarily stores the information in a memory incorporated in the semiconductor device capable of wireless communication. Information that is read by a reader is temporarily stored in the reader and then transmitted to an automatic urinalysis apparatus (packet communication). Then, the information goes thorough an analysis apparatus and is given an analysis result, which is added to a database of each patient.

In recent years, test papers are sold by various manufacturers. However, because their judgment values differ, the urinalysis standardization committee of Japanese Committee for Clinical Laboratory Standards (JCCLS) is working on standardization of sugar, protein, and occult blood of urinalysis paper. The present examination apparatus preferably is an examination apparatus using the above standards.

Further, in addition to urinalysis, by changing sensitivity or the like of the test paper, the reagent portion, or the photo sensor, it is possible to examine and obtain data on various liquids. For example, the examination apparatus can be applied various fields such as blood tests and water quality tests, and examination can be improved in quickness and efficiency.

In the chip 105, a photo sensor (photoelectric conversion device) 202 as a sensor, a semiconductor device 201 capable of wireless communication, and a light emitting diode (LED) 203 as a light source (see FIG. 2A) are provided. If necessary, an RF (Radio Frequency) battery 204 may be placed as means for supplying power to each element (see FIG. 2B). Note that only one of the LED 104 and the LED 203 may be provided. However, the LED 104 and the LED 203 do not have to be provided as described below.

Figure 2A:
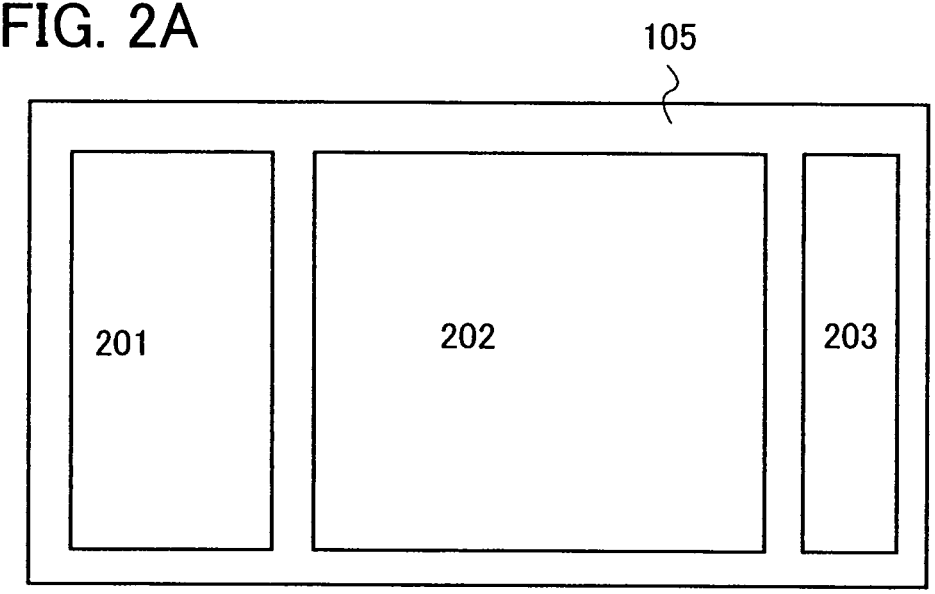
FIGS. 2A and 2B are block diagrams each showing an examination element of the present invention.
Figure 2B:
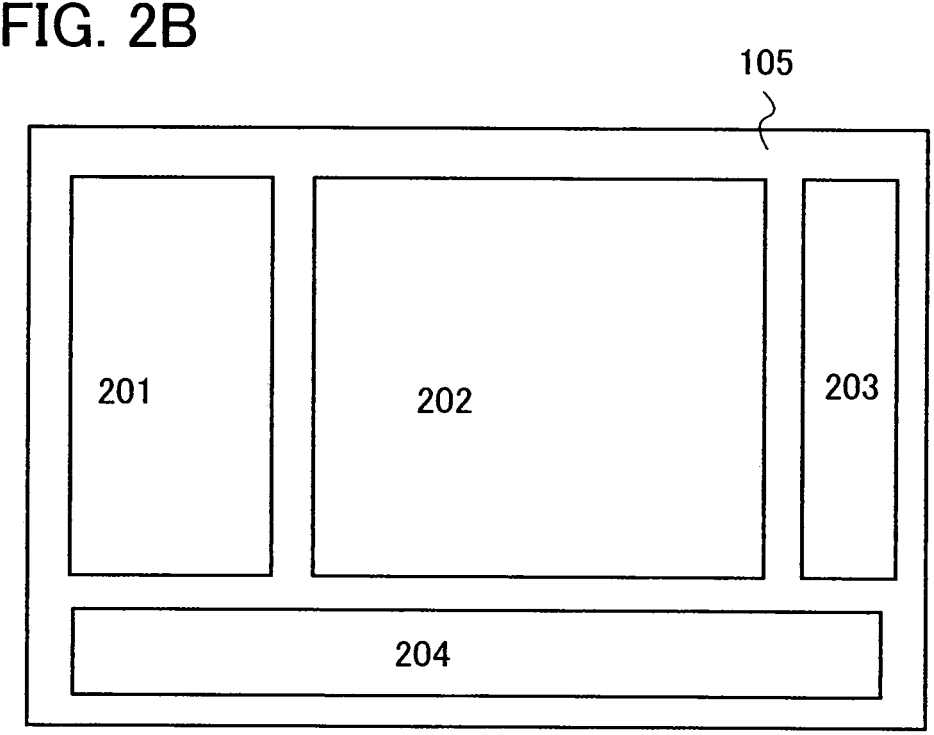
Figure 3A:
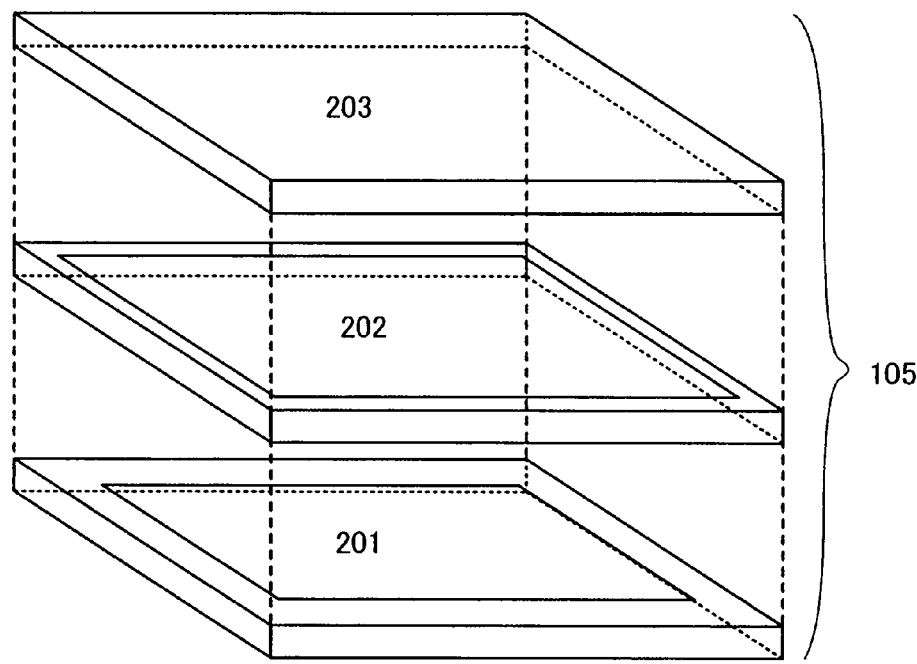
FIGS. 3A and 3B are block diagrams each showing an examination element of the present invention.
Figure 3B:
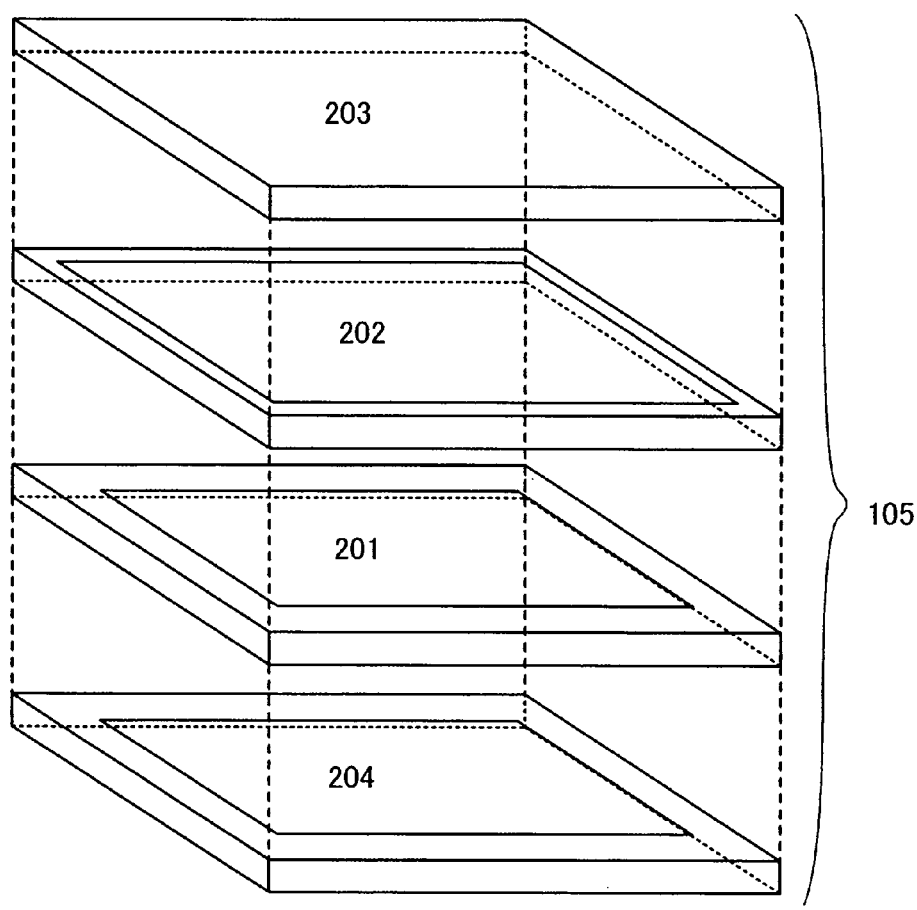

In FIG. 2A, the photo sensor 202, the semiconductor device 201 capable of wireless communication, and the LED 203, are placed over the same flat surface, and in FIG. 2B, the photo sensor 202, the semiconductor device 201 capable of wireless communication, the LED 203, and the battery 204 are placed over the same flat surface. However, the chip 105 may be formed by forming each of them over separate substrates and then attaching them together. FIG. 3A shows the chip 105 obtained by attaching together the semiconductor device 201 capable of wireless communication, the photo sensor 202, and the LED 203, and FIG. 3B shows the chip 105 obtained by attaching together the semiconductor device 201 capable of wireless communication, the photo sensor 202, the LED 203, and the battery 204. An order of stacking the semiconductor device 201 capable of wireless communication, the photo sensor 202, the LED 203, and the battery 204 does not have to be that shown in FIG. 3A to FIG. 3B. A through-hole is provided in each substrate and the substrate is electrically connected to each other with a conductive material. In addition, the LED 203 may be surface-emitting.

Further, the LED 104 and the LED 203 do not have to be provided if sufficient light that can be detected by the photo sensor 202 is obtained. Alternatively, a bottom surface or the entire surface of the container 111 may be formed of a light transmitting material, and detection by the photo sensor 202 may be performed by taking in light from a light source provided outside of the examination element 101 through a region of the container 111 formed of the light transmitting material.

Figure 4A:
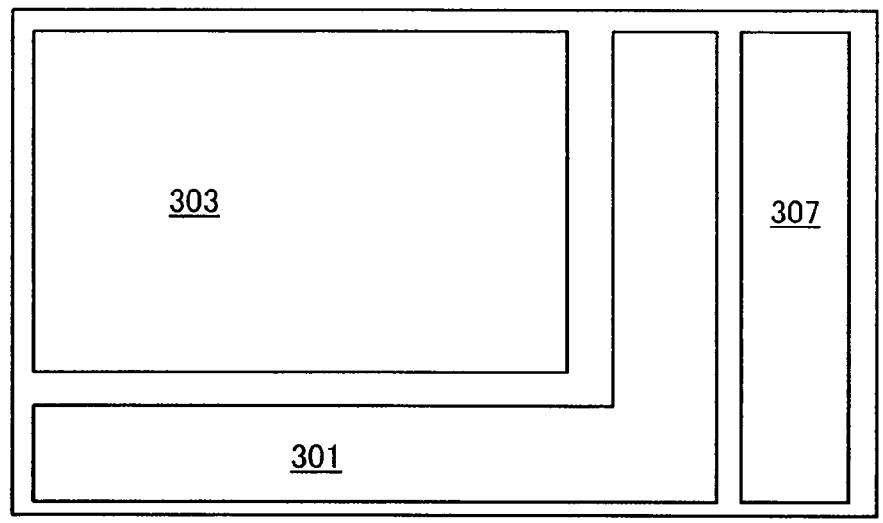
FIGS. 4A and 4B are a block diagram and a circuit diagram of a photo sensor, respectively.
Figure 4B:
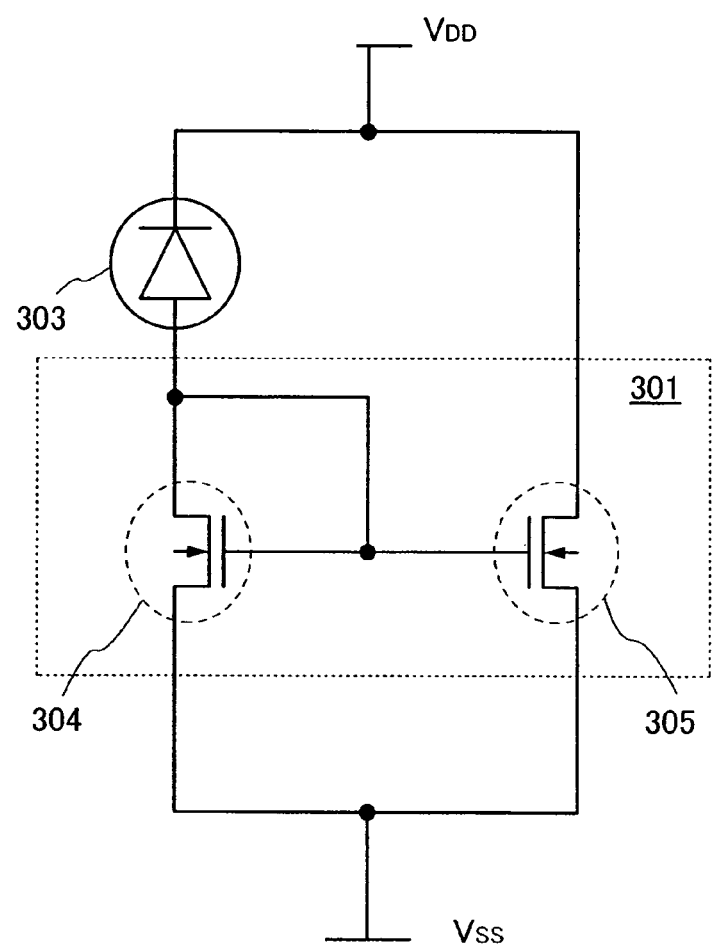

The photo sensor 202 is described with reference to FIGS. 4A to 5, and FIGS. 7A to 11B. The photo sensor 202 of this embodiment mode includes a photo diode 303 and an amplifier circuit 301 that amplifies an output current (light current) of the photo diode 303. FIG. 4A and FIG. 4B show a top view and a circuit diagram of the photo sensor 202, respectively. Note that a circuit 307 may be additionally provided as necessary. The circuit 307 may be for example a processing circuit that processes and converts an output current into a signal that is sent to the semiconductor device 201 capable of wireless communication, a signal processing circuit that reads an output from the photo diode 303, a communication circuit that outputs an output from the signal processing circuit to an external device, and the like.

In this embodiment mode, a current mirror circuit is used as the amplifier circuit 301, and as a basic structure thereof, a thin film transistor (TFT) 304 and a TFT 305 are provided on a reference side and on an amplification side, respectively.

In FIG. 4B, a gate electrode of the TFT 304 included in the current mirror circuit 301 is electrically connected to a gate electrode of the other TFT 305 included in the current mirror circuit 301. Further, the gate electrode of the TFT 304 is also electrically connected to a drain electrode (also called a "drain terminal") that is one of a source electrode or drain electrode of the TFT 304.

The drain terminal of the TFT 304 is electrically connected to the photo diode 303, a drain terminal of the TFT 305, and a high potential power supply $V_{DD}$.

A source electrode that is the other of the source electrode or drain electrode of the TFT 304 is electrically connected to a low potential power supply $V_{SS}$ and a source terminal of the TFT 305.

In FIG. 4B, the gate electrode of the TFT 305 included in the current mirror circuit 301 is electrically connected to the gate electrode and the drain terminal of the TFT 304.

Also, a common potential is applied to the gate electrodes of the TFT 304 and the TFT 305 since they are connected to each other.

FIG. 4B shows an example of the current mirror circuit including two TFTs. At this time, in a case where the TFT 304 and the TFT 305 have the same characteristic, the ratio of a reference current and an output current is 1:1.

Figure 7A:
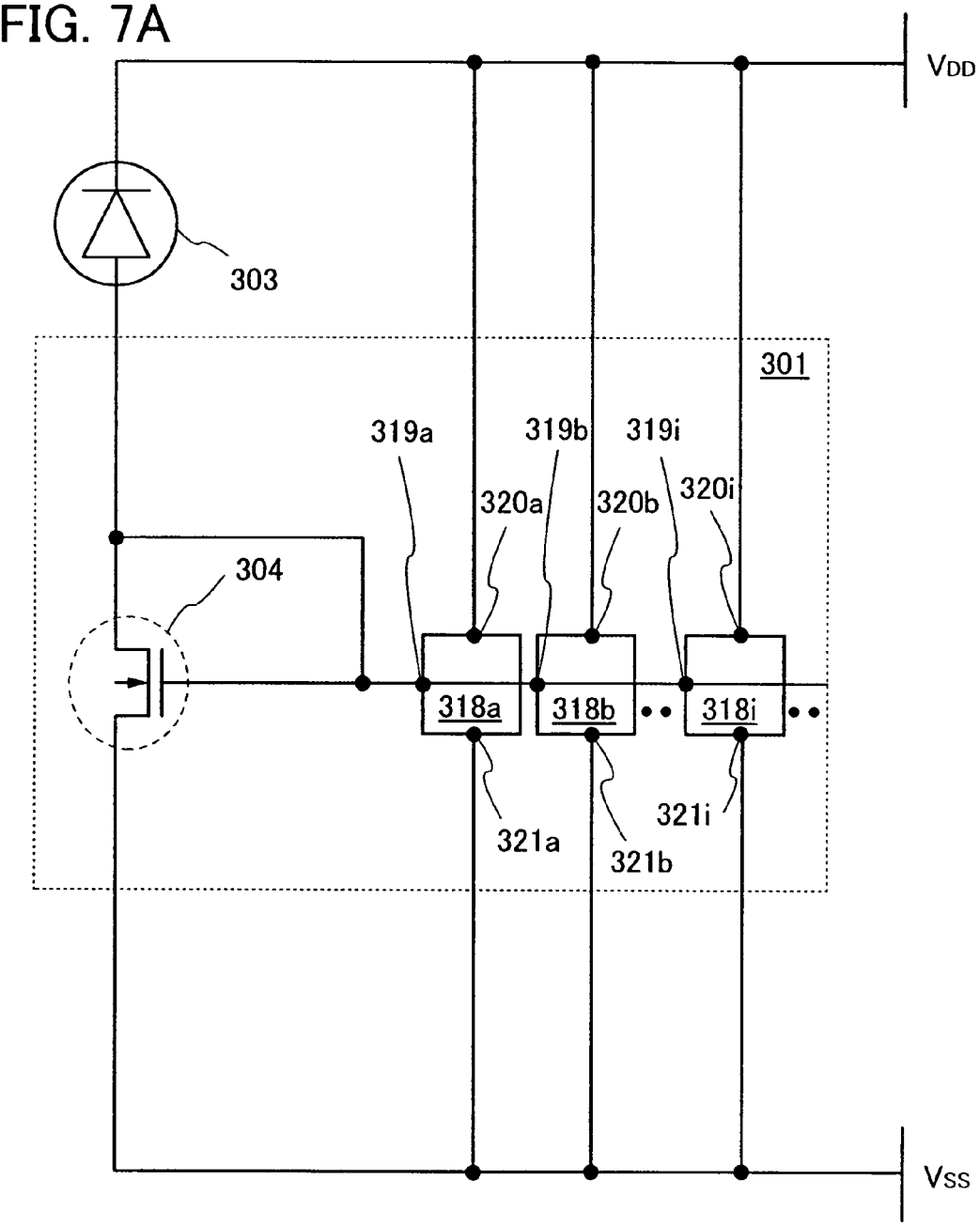
FIGS. 7A and 7B are circuit diagrams each showing a photo sensor of the present invention.
Figure 7B:
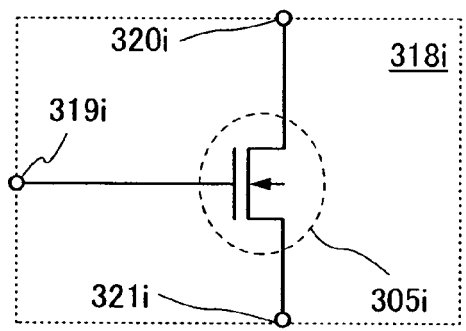

Circuit structures for making an output value increase by n folds is shown in FIGS. 7A and 7B. The circuit structure of FIG. 7A corresponds to that in FIG. 4B with n number of TFT 305. As shown in FIG. 7A, by making the ratio of the n-channel TFT 304 and the n-channel TFT 305 be 1:n, the output value can increase by n folds. This is because of the same principle as increasing a channel width W of the TFT and making an allowable amount of current that can be fed to the TFT increase by n folds.

For example, in a case of designing the output value to increase by 100 folds, a target current can be obtained by connecting one n-channel TFT 304 and 100 n-channel TFTs 305 in parallel.

A detailed circuit structure of a circuit 318i (a circuit 318a, a circuit 318b, or the like) in FIG. 7A is shown in FIG. 7B.

The circuit structure in FIG. 7B is based on the circuit structures in FIGS. 4B and 7A, and the same elements are denoted by the same reference numerals. That is, a gate electrode of a TFT 305i is electrically connected to a terminal 319i, and a drain terminal of the TFT 305ii is electrically connected to a terminal 320i. Also, a source terminal of the TFT 305i is electrically connected to a terminal 321i.

Note that in order to describe the circuit 318a, the circuit 318b, and the like in FIG. 7A, the circuit 318i, which is one of them, is shown in FIG. 7B. Since the circuit structure of the circuit 318i is based on those of FIGS. 4B and 7A, reference numerals in FIG. 7B with an "i" at the end correspond to those with reference numerals in FIG. 4B without the "i." That is, for example, the TFT 305 in FIG. 4B is the same TFT as the TFT 305i in FIG. 7B.

Therefore, in FIG. 7A, the n-channel TFT 305 includes n number of n-channel TFTs 305a, 305b, 305i, and the like. Accordingly, a current that flows through the TFT 304 is amplified by n folds and output.

Note that in FIGS. 7A and 7B, when the same elements as those in FIG. 4B are referred to, the same reference numerals are used.

Further, although in FIG. 4B, the current mirror circuit 301 is shown as an equivalent circuit using an n-channel TFT, a p-channel TFT may be used instead of the n-channel TFT.

Figure 8:
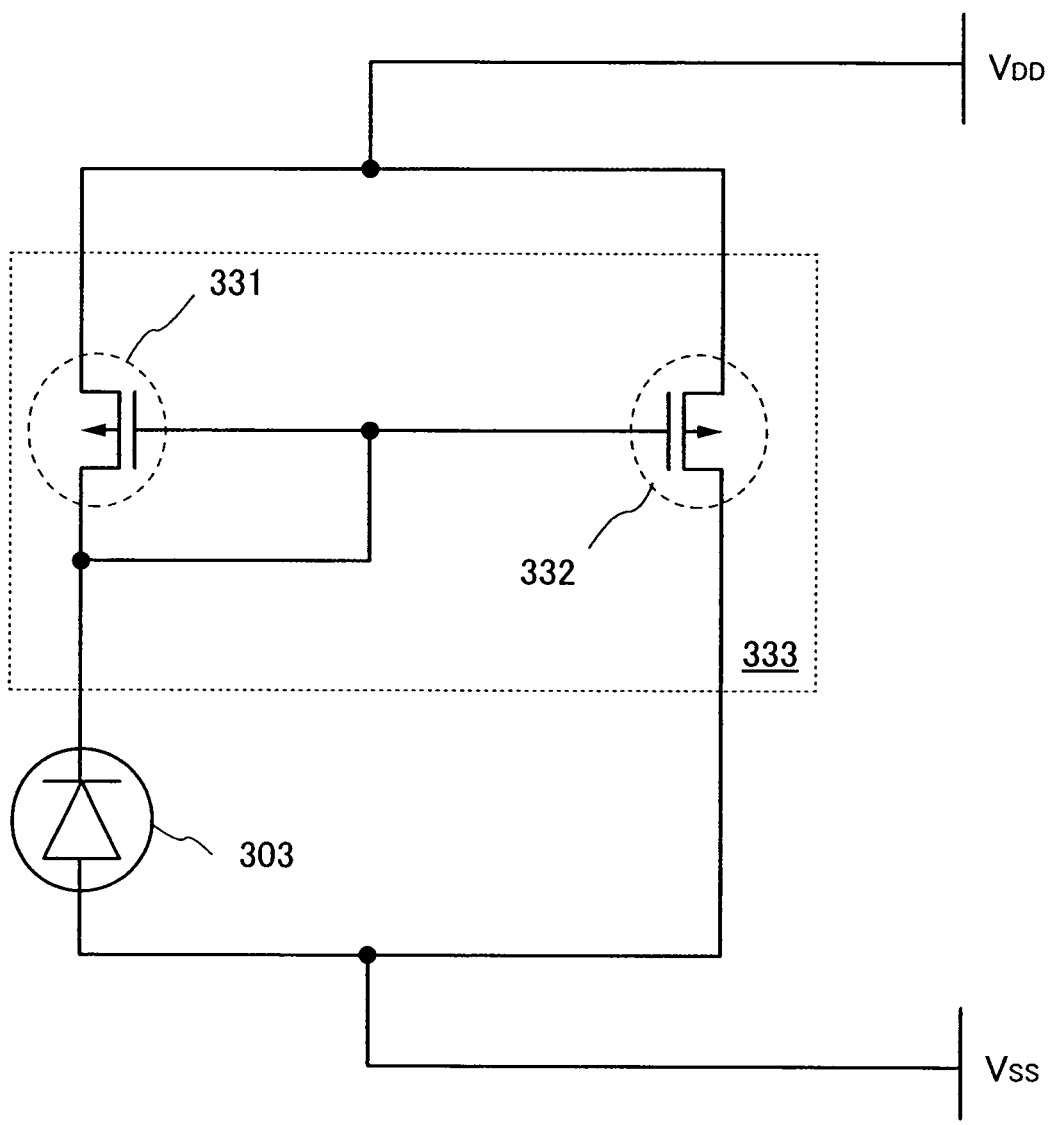
FIG. 8 is a circuit diagram showing a photo sensor of the present invention.

In a case of forming the amplifier circuit with a p-channel TFT, the amplifier circuit becomes the equivalent circuit shown in FIG. 8. As shown in FIG. 8, a current mirror circuit 333 includes p-channel TFTs 331 and 332. Note that elements in FIG. 4B that are the same as those in FIG. 8 are shown by the same reference numerals.

Figure 5:
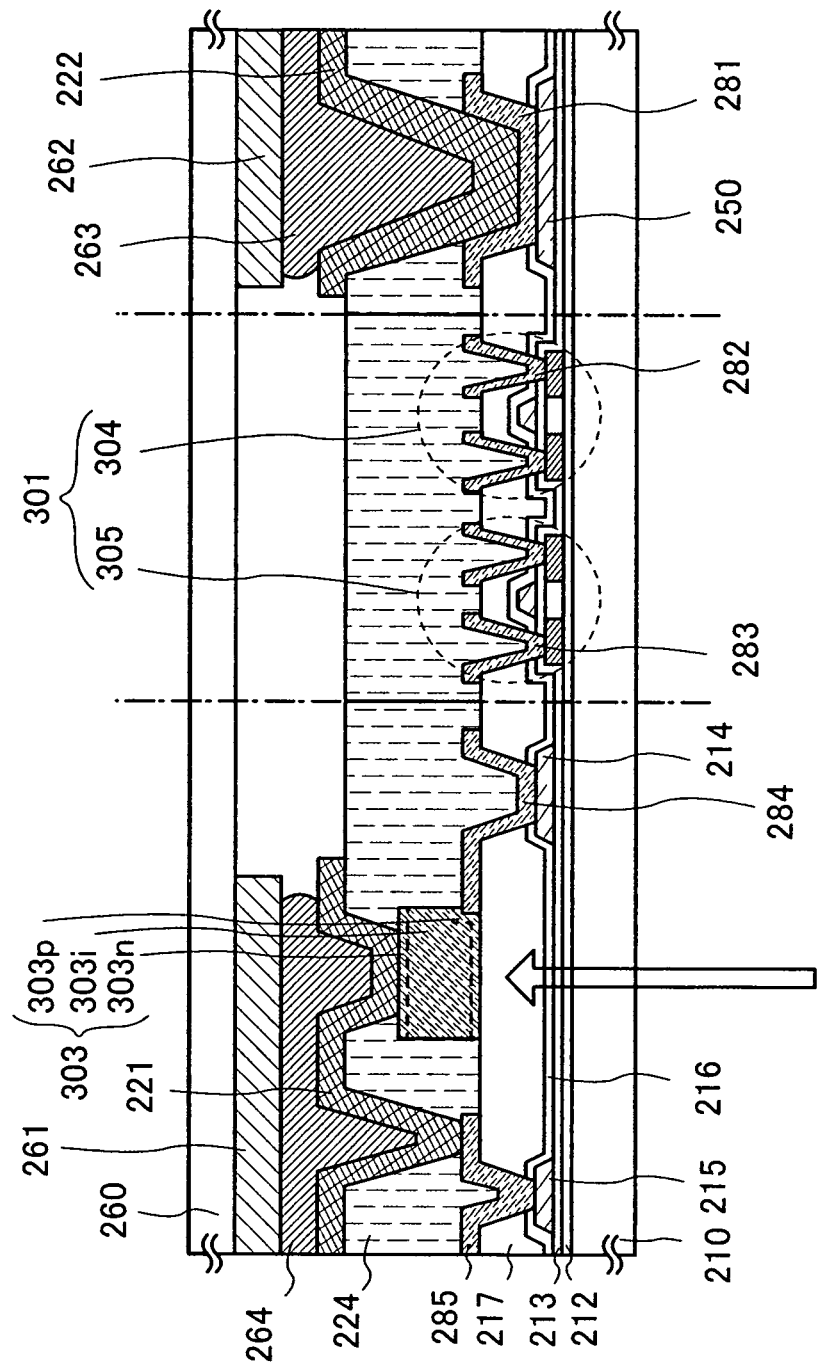
FIG. 5 is a cross-sectional diagram showing a photo sensor of the present invention.

FIG. 5 shows a cross-sectional diagram of a circuit including the current mirror circuit 301 including the TFTs 304 and 305, and the photo diode 303 in FIG. 4B.

FIG. 5 shows a substrate 210, a base insulating film 212, and a gate insulating film 213.

In addition, a connection electrode 285, a terminal electrode 281, source or drain electrodes 282 of a TFT 304, and source or drain electrodes 283 of a TFT 305 each have a stacked-layer structure of a refractory metal film and a low resistance metal film (an aluminum alloy, pure aluminum, or the like). Here, the source or drain electrodes 282 and 283 are each formed to have a three-layer structure where a titanium film (Ti film), an aluminum film (Al film), and a Ti film are sequentially stacked.

Each of the connection electrode 285, the terminal electrode 281, the source or drain electrodes 282 of the TFT 304, and the source or drain electrodes 283 of the TFT 305 has a stacked-layer structure of a refractory metal film and a low resistance metal film.

As such a low resistance metal film, an aluminum alloy, pure aluminum, or the like can be given. In this embodiment mode, a three-layer structure where a titanium film (Ti film), an aluminum film (Al film), and a Ti film are sequentially stacked is employed as such a stacked-layer structure of a refractory metal film and a low-resistance metal film.

Instead of the stacked-layer structure of the refractory metal film and the low resistance metal film, the connection electrode 285, the terminal electrode 281, the source or drain electrodes 282 of the TFT 304, and the source or drain electrodes 283 of the TFT 305 can also be each formed of a single-layer conductive film. As such a single-layer conductive film, a single-layer film formed of an element of titanium (Ti), tungsten (W), tantalum (Ta), molybdenum (Mo), neodymium (Nd), cobalt (Co), zirconium (Zr), zinc (Zn), ruthenium (Ru), rhodium (Rh), palladium (Pd), osmium (Os), iridium (Ir), and platinum (Pt) or an alloy material or a compound material containing the element as its main component; or a single-layer film formed of a nitride thereof, for example, titanium nitride, tungsten nitride, tantalum nitride, or molybdenum nitride can be used.

Also, in FIG. 5, although an example is shown in which the n-channel TFTs 304 and 305 are top gate TFTs with a structure including one channel forming region (called a "single gate structure" in this specification), the n-channel TFTs 304 and 305 may have a structure including a plurality of channel forming regions to reduce variations in on-current values.

In order to reduce the value of off-current, a lightly doped drain (LDD) region may also be provided in the n-channel TFTs 304 and 305. An LDD region is a region to which an impurity element is added at low concentration between a channel formation region and a source or drain region that is formed by being added with an impurity element at high concentration. By providing the LDD region, there is an effect of relieving an electric field in the vicinity of the drain region to prevent deterioration due to hot carrier injection.

In addition, in order to prevent deterioration of the value of an on-current due to hot carriers, the n-channel TFTs 304 and 305 may employ a structure in which an LDD region and a gate electrode are placed so as to be overlapped with each other with a gate insulating film therebetween(referred to as a "GOLD (Gate-drain Overlapped LDD) structure" in this specification).

In a case of where a GOLD structure is employed, the effect of reducing an electric field in the vicinity of a drain region and to prevent deterioration due to hot carrier injection is more enhanced than in a case where an LDD region and a gate electrode are not overlapped with each other. By employing of such a GOLD structure, electric field intensity in the vicinity of a drain region is relieved and hot carrier injection is prevented; therefore, it is effective for preventing a deterioration phenomenon.

The TFTs 304 and 305 that form the current mirror circuit 301 may also be a bottom gate TFT, for example, an inversely staggered TFT as well as a top gate TFT.

In addition, a wiring 215 is connected to the drain wiring (also referred to as a "drain electrode") or the source wiring (also referred to as a "source electrode") of the TF 304. Also, an insulating film 216, an insulating film 217, and a connection electrode 285 are included. Note that, as the insulating film 217, a silicon oxide film that is formed by a CVD method is preferably used. When the insulating film 217 is formed of a silicon oxide film that is formed by a CVD method, fixing intensity is improved.

In addition, a terminal electrode 250 is formed in the same process as the wiring 215, and the terminal electrode 281 is formed in the same process as the connection electrode 285.

Moreover, a terminal electrode 221 is mounted on an electrode 261 of a substrate 260 with a solder 264. A terminal electrode 222 is formed in the same process as the terminal electrode 221, and is mounted on an electrode 262 of the substrate 260 with a solder 263.

A process of manufacturing a semiconductor device containing the current mirror circuit 301 that includes the photo diode 303 and the TFTs 304 and 305 is described below with reference to FIG. 5 and FIGS. 9A to 11B.

First, an element is formed over a substrate (the first substrate 210). Here, as the substrate 210, an alkali-free glass substrate is used, which is one type of glass substrate and is commercially available.

Next, a silicon oxide film containing nitrogen (100 nm thick) to be a base insulating film 212 is formed by a plasma CVD method, and further, without being exposed to the atmosphere, a semiconductor film, for example, an amorphous silicon film containing hydrogen (54 nm thick) is formed and stacked thereover. In addition, the base insulating film 212 may also be formed using the stack of a silicon oxide film, a silicon nitride film, and a silicon oxide film containing nitrogen. For example, as the base insulating film 212, a film may also be formed where a silicon nitride film containing oxygen with thickness of 50 nm, and further, a silicon oxide film containing nitrogen with a thickness of 100 nm are stacked. Note that the silicon oxide film containing nitrogen or the silicon nitride film serves as a blocking layer that prevents diffusion of an impurity such as an alkaline metal from the glass substrate.

Then, the amorphous silicon film is crystallized by a solid phase growth method, a laser crystallization method, a crystallization method using a catalytic metal, or the like to form a semiconductor film having a crystal structure (a crystalline semiconductor film), for example, a polycrystalline silicon film. Here, a polycrystalline silicon film is obtained by a crystallization method using a catalytic element. A solution containing 10 ppm of nickel in weight conversion is added to the surface of the amorphous silicon film using a spinner. Note that a method in which a nickel element is diffused over the entire surface by a sputtering method may also be used instead of the addition method with a spinner. Then, a heating treatment is performed and crystallization is performed to form a semiconductor film having a crystal structure (here, a polycrystalline silicon film). Here, after the heating treatment (at 500 □C for an hour), a heating treatment for crystallization (at 550° C. for 4 hours) is performed to obtain a polycrystalline silicon film.

Subsequently, an oxide film over the surface of the polycrystalline silicon film is removed with a dilute hydrofluoric acid or the like. Thereafter, laser beam irradiation for increasing a degree of crystallization and repairing a defect left in the crystal grain is performed.

Note that the following laser irradiation method may also be employed in a case where a crystalline semiconductor film is obtained by crystallization of an amorphous silicon film by a laser crystallization method or in a case where laser irradiation is performed to repair a defect left in the crystal grain after a semiconductor film having a crystal structure is obtained.

A continuous wave laser beam (CW laser beam) or a pulsed wave laser beam (pulsed laser beam) can be used for the laser irradiation. As the laser beam that can be used here, a beam emitted from one or more of a gas laser such as an Ar laser, a Kr laser, or an excimer laser; a laser using, as a medium, single crystalline YAG, YVO$_4$, forsterite (Mg$_2$SiO$_4$), YAlO$_3$, or GdVO$_4$ or polycrystalline (ceramic) YAG, Y$_2$O$_3$, YVO$_4$, YAlO$_3$, or GdVO$_4$ doped with one or more of Nd, Yb, Cr, Ti, Ho, Er, Tm, and Ta as a dopant; a glass laser; a ruby laser; an alexandrite laser; a Ti:sapphire laser; a copper vapor laser; and a gold vapor laser can be used. A crystal with a large grain size can be obtained by irradiation of a laser beam having a fundamental wave of such lasers or one of second, third, and fourth harmonic of the fundamental wave. For example, the second harmonic (532 nm) or the third harmonic (355 nm) of an Nd:YVO$_4$ laser (fundamental wave of 1064 nm) can be used. In this case, an energy density of approximately 0.01 to 100 MW/cm$^2$ (preferably, 0.1 to 10 MW/cm$^2$) is required for a laser. The scanning speed is set at approximately 10 to 2000 cm/sec for the irradiation.

Note that a laser using, as a medium, single crystalline YAG, YVO$_4$, forsterite (Mg$_2$SiO$_4$), YAlO$_3$, or GdVO$_4$ or polycrystalline (ceramic) YAG, Y$_2$O$_3$, YVO$_4$, YAlO$_3$, or GdVO$_4$ doped with one or more of Nd, Yb, Cr, Ti, Ho, Er, Tm, and Ta as a dopant; an Ar ion laser; a Kr ion laser; or a Ti:sapphire laser can be continuously oscillated. Further, pulse oscillation thereof can be performed with a repetition rate of 10 MHz or more by performing a Q switch operation or mode synchronization. When a laser beam is oscillated with a repetition rate of 10 MHz or more, a semiconductor film is irradiated with a subsequent pulse while the semiconductor film is melted by the laser and solidified. Therefore, unlike in a case of using a pulsed laser with a low repetition rate, a solid-liquid interface can be continuously moved in the semiconductor film so that crystal grains that continuously grow toward a scanning direction can be obtained.

When ceramic (polycrystal) is used as a medium, the medium can be formed to have a free shape in a short time at low cost. When a single crystal is used, a columnar medium with several mm in diameter and several tens of mm in length is usually used. In the case of using the ceramic, a medium bigger than the case of using the single crystal can be formed.

A concentration of a dopant such as Nd or Yb in a medium, which directly contributes to light emission, cannot be changed largely in both cases of the single crystal and the polycrystal; therefore, there is a limitation to some extent in improving output of a laser by increase in concentration. However, in the case of the ceramics, the size of the medium can be significantly increased as compared with the case of the single crystal; therefore, the output is improved drastically.

Further, in the case of the ceramic, a medium with a parallel six-hedron shape or a rectangular shape can be easily formed. In a case of using a medium having such a shape, when oscillated light is made to zigzag inside the medium, a long path of the oscillated light can be obtained. Therefore, amplitude is increased and a laser beam can be oscillated at high output. Moreover, since a cross-sectional shape of a laser beam, which is emitted from a medium having such a shape, is a quadrangular shape, as compared with a laser beam with a circular shape, the laser beam with the quadrangular shape in cross section has an advantage to be shaped into a linear beam. By shaping a laser beam emitted in the above manner using an optical system, a linear beam with 1 mm or less in length of a short side and several mm to several m in length of a long side can be easily obtained. Further, when a medium is evenly irradiated with excited light, a linear beam is emitted with an even energy distribution in a long side direction.

When a semiconductor film is irradiated with such a linear beam, an entire surface of the semiconductor film can be annealed evenly. When even annealing is required from one end to the other end of the linear beam, a devisal of disposing slits on both ends of the linear beam, to shield an attenuated portion of energy from light, or the like is required.

In a case where the laser irradiation is performed in the atmosphere or an oxygen atmosphere, an oxide film is formed over the surface by laser beam irradiation.

Next, in addition to the oxide film formed by the laser beam irradiation, a barrier layer formed of an oxide film having a thickness of 1 to 5 nm in total is formed by treatment of the surface with ozone water for 120 seconds. The barrier layer is formed in order to remove a catalyst element, which is added for crystallization, for example, nickel (Ni) from the film. Although the barrier layer is formed using ozone water here, a barrier layer may also be formed by deposition of an oxide film having a thickness of approximately 1 to 10 nm using a method for oxidizing a surface of a semiconductor film having a crystal structure by UV-ray irradiation under an oxygen atmosphere; a method for oxidizing a surface of a semiconductor film having a crystal structure by oxygen plasma treatment; a plasma CVD method; a sputtering method; an evaporation method; or the like. In addition, before the barrier layer is formed, the oxide film formed by laser beam irradiation may also be removed.

Then, over the barrier layer, an amorphous silicon film containing argon is formed to have a thickness of 10 to 400 nm, for example 100 nm here, by a sputtering method to serve as a gettering site. Here, the amorphous silicon film containing argon is formed under an atmosphere containing argon using a silicon target. When a plasma CVD method is used to form the amorphous silicon film containing argon, the deposition condition is as follows: a flow ratio of monosilane to argon (SiH$_4$:Ar) is set at 1:99; a deposition pressure, 6.665 Pa; a RF power density, 0.087 W/cm$^2$; and a deposition temperature, 350° C.

Thereafter, a furnace heated at 650° C. is used for heat treatment for three minutes to remove a catalyst element (gettering). By this treatment, the catalyst element concentration in the semiconductor film having a crystal structure is reduced. A lamp annealing apparatus may also be used instead of the furnace.

Subsequently, the amorphous silicon film containing an argon element, which is a gettering site, is selectively removed with the barrier layer as an etching stopper, and then, the barrier layer is selectively removed with dilute hydrofluoric acid. Note that there is a tendency that nickel is likely to move to a region with a high oxygen concentration in gettering; thus, it is desirable that the barrier layer made of the oxide film be removed after gettering.

Note that, when crystallization of a semiconductor film using a catalytic element is not performed, the above steps such as the formation of the barrier layer, the formation of the gettering site, the heat treatment for gettering, the removal of the gettering site, and the removal of the barrier layer are not necessary.

Next, after a thin oxide film is formed with ozone water over the surface of the obtained semiconductor film having a crystal structure (for example, a crystalline silicon film), a mask made of a resist is formed using a first photomask. Then, an etching treatment is performed to obtain a desired shape, thereby forming semiconductor films 231 and 232 separated in island shapes (referred to as an "island-shaped semiconductor region" in this specification) (see FIG. 9A). After the island-shaped semiconductor regions are formed, the mask made of resist is removed.

Then, if necessary, doping of an impurity element (boron or phosphorus) in a minute amount is performed to control the threshold value of a TFT. Here, an ion doping method is used, in which diborane (B$_2$H$_6$) is not separated by mass but excited by plasma.

Subsequently, the oxide film is removed with an etchant containing hydrofluoric acid, and at the same time, the surfaces of the island-shaped semiconductor regions 231 and 232 are washed. Thereafter, an insulating film containing silicon as its main component, which is to serve as a gate insulating film 213, is formed. Here, a silicon oxide film containing nitrogen (composition ratio: Si=32%, O=59%, N=7%, and H=2%) is formed to have a thickness of 115 nm by a plasma CVD method.

Figure 9A:
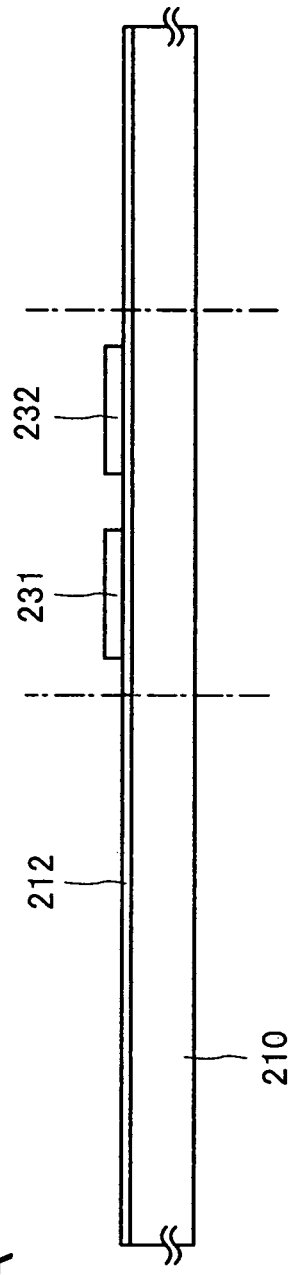
FIGS. 9A to 9C are diagrams showing a manufacturing process of a photo sensor of the present invention.
Figure 9B:
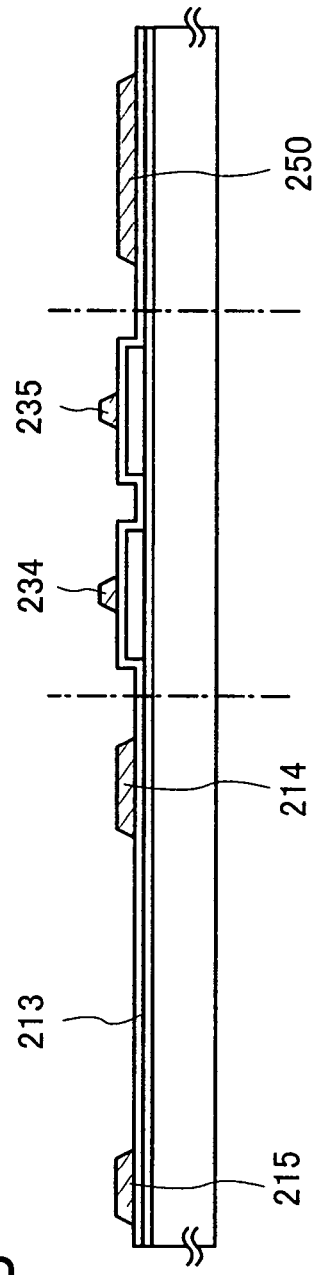
Figure 9C:
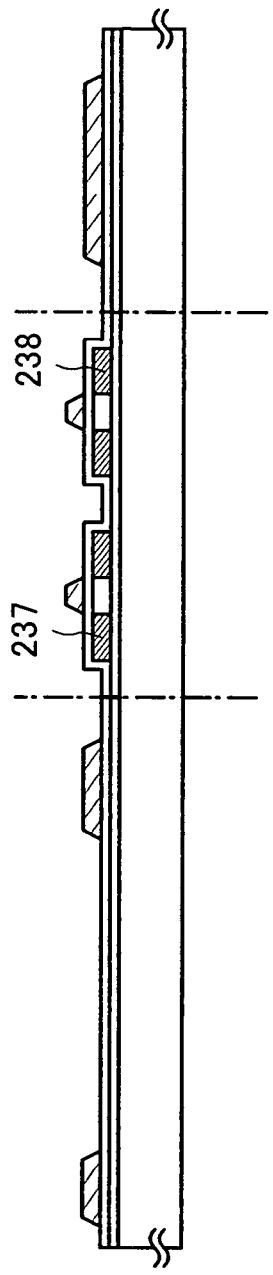

Next, after a metal film is formed over the gate insulating film 213, a gate electrode 234 and a gate electrode 235, a wiring 214 and a wiring 215, and a terminal electrode 250 are formed (see FIG. 9B).

In addition, as the gate electrodes 234 and 235, the wirings 214 and 215, and the terminal electrode 250, a single-layer film formed of an element selected from titanium (Ti), tungsten (W), tantalum (Ta), molybdenum (Mo), neodymium (Nd), cobalt (Co), zirconium (Zr), zinc (Zn), ruthenium (Ru), rhodium (Rh), palladium (Pd), osmium (Os), iridium (Ir), platinum (Pt), aluminum (Al), gold (Au), silver (Ag), and copper (Cu) or an alloy material or a compound material containing the element as its main component. Alternatively, a single-layer film formed of a nitride thereof, for example, titanium nitride, tungsten nitride, tantalum nitride, or molybdenum nitride can be used.

Moreover, a stacked-layer film may also be used instead of the above single-layer film. For example, as the gate electrode 234 and the gate electrode 235, the wiring 214 and the wiring 215, and the terminal electrode 250, a film may also be used where tantalum nitride (TaN) and tungsten (W) with thicknesses of 30 nm and 370 nm, respectively, are stacked.

Next, an impurity imparting one conductivity type is introduced to the island-shaped semiconductor region 231 and the island-shaped semiconductor region 232 to form source or drain regions 237 of a TFT 305 and source or drain regions 238 of a TFT 304. An n-channel TFT is formed in this embodiment mode; therefore, an n-type impurity, for example, phosphorus (P) or arsenic (As) is introduced to the island-shaped semiconductor region 231 and the island-shaped semiconductor region 232 (see FIG. 9C).

Then, after a first interlayer insulating film including a silicon oxide film (not shown) is formed to have a thickness of 50 nm by a CVD method, a step of an activation treatment of an impurity element added to each island-shaped semiconductor region is carried out. This activation step is performed by a rapid thermal annealing method (RTA method) using a lamp light source, an irradiation method of a YAG laser or an excimer laser from the back side, a heat treatment using a furnace, or a method that is combined with any one of the above methods.

Subsequently, a second interlayer insulating film 216 including a silicon nitride film containing hydrogen and oxygen is formed, for example, with a thickness of 10 nm.

Figure 10A:
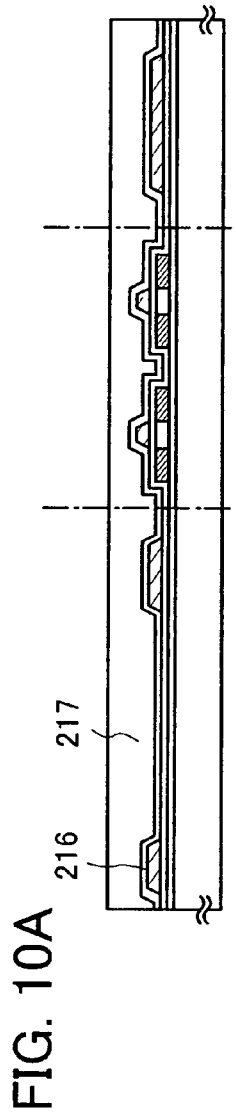
FIGS. 10A to 10C are diagrams showing a manufacturing process of a photo sensor of the present invention.

Next, a third interlayer insulating film 217 formed of an insulator material is formed over the second interlayer insulating film 216 (see FIG. 10A). An insulating film obtained by a CVD method can be used for the third interlayer insulating film 217. In this embodiment mode, in order to improve adhesiveness, a silicon oxide film containing nitrogen is formed with a thickness of 900 nm as the third interlayer insulating film 217.

Then, a heat treatment (heat treatment at a temperature of 300 to 550° C. for 1 to 12 hours, for example, at 410° C. for one hour in a nitrogen atmosphere) is performed to hydrogenate the island-shaped semiconductor films. This step is performed to terminate a dangling bond in the island-shaped semiconductor films by hydrogen contained in the second interlayer insulating film 216. The island-shaped semiconductor films can be hydrogenated regardless of whether the gate insulating film 213 is formed.

In addition, as the third interlayer insulating film 217, an insulating film using siloxane and a stacked structure thereof can also be used. Siloxane is composed of a skeleton structure of a bond of silicon (Si) and oxygen (O). For a substituent, a compound containing at least hydrogen (for example, an alkyl group or an aromatic hydrocarbon) is used. Fluorine may also be used for the substituent. Moreover, a compound containing at least hydrogen and fluorine may also be used for the substituent.

When an insulating film using siloxane and a stacked structure thereof are used as the third interlayer insulating film 217, after the second interlayer insulating film 216 is formed, a heat treatment for hydrogenating the island-shaped semiconductor films can be performed, and then, the third interlayer insulating film 217 can also be formed.

Next, a mask made of a resist is formed, and the first interlayer insulating film, the second interlayer insulating film 216, and the third interlayer insulating film 217, or the gate insulating film 213 are selectively etched to form contact holes. Then, the mask made of a resist is removed.

Note that the third interlayer insulating film 217 may be formed as necessary. In a case of not forming the third interlayer insulating film 217, after the second interlayer insulating film 216 is formed, the first interlayer insulating film, the second interlayer insulating film 216, and the gate insulating film 213 are selectively etched to form contact holes.

Figure 10B:
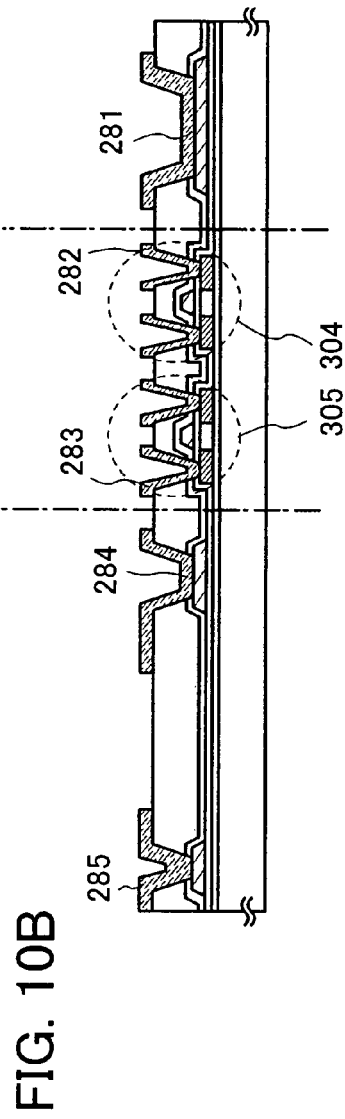

Then, after a metal stacked film is formed by a sputtering method, a mask made of resist is formed, and then, the metal film is selectively etched to form a wiring 284, a connection electrode 285, a terminal electrode 281, source or drain electrodes 282 of the TFT 304, and source or drain electrodes 283 of the TFT 305 (see FIG. 10B).

In FIG. 10B, the wiring 284, the connection electrode. 285, the terminal electrode 281, the source or drain electrodes 282 of the TFT 304, and the source or drain electrodes 283 of the TFT 305 are each formed of a single-layer conductive film.

As such a single-layer film, a titanium film (Ti film) is preferable in terms of heat resistance, conductivity, and the like. Instead of the titanium film, a single-layer film formed of an element of tungsten (W), tantalum (Ta), molybdenum (Mo), neodymium (Nd), cobalt (Co), zirconium (Zr), zinc (Zn), ruthenium (Ru), rhodium (Rh), palladium (Pd), osmium (Os), iridium (Ir), and platinum (Pt) or an alloy material or a compound material containing the element as its main component; or a single-layer film formed of a nitride thereof, for example, titanium nitride, tungsten nitride, tantalum nitride, or molybdenum nitride can be used. The number of deposition can be reduced in the manufacturing process by formation of the following components into a single-layer film: the wiring 284, the connection electrode 285, the terminal electrode 281, the source or drain electrodes 282 of the TFT 304, and the source or drain electrodes 283 of the TFT 305.

Figure 10C:
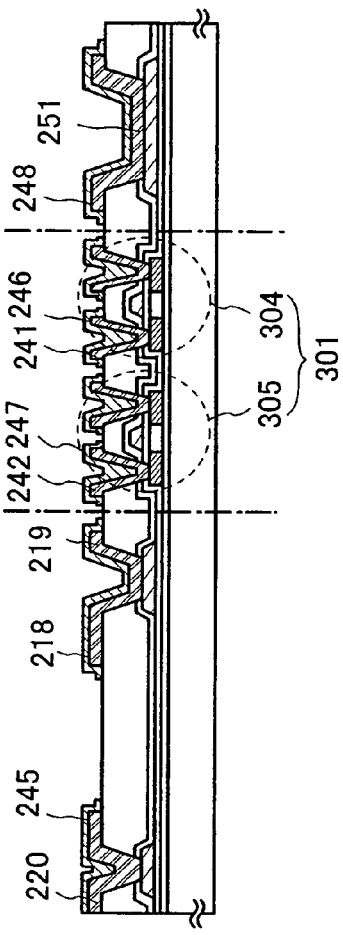

In addition, FIG. 10C shows a case where a wiring 219, a connection electrode 220, a terminal electrode 251, source or drain electrodes 241 of the TFT 304, and source or drain electrodes 242 of the TFT 305 are each provided with a protective electrode.

First, lower conductive films of the wiring 219, the connection electrode 220, the terminal electrode 251, the source or drain electrodes 241 of the TFT 304, and the source or drain electrodes 242 of the TFT 305 each have a stacked-layer structure of a refractory metal film and a low-resistance metal film (an aluminum alloy, pure aluminum, or the like). Here, the lower conductive film of the wiring 219, and the source or drain electrodes 241 and 242 each have a three-layer structure where a titanium film (Ti film), an aluminum film (Al film), and a Ti film are sequentially stacked.

Further, protective electrodes 218, 245, 248, 246, and 247 are formed so as to cover the wiring 219, the connection electrode 220, the terminal electrode 251, the source or drain electrodes 241 of the TFT 304, and the source or drain electrodes 242 of the TFT 305, respectively.

In etching a photoelectric conversion layer 303, the wiring 219 is protected by the protective electrode 218 covering the wiring 219. A material for the protective electrode 218 is preferably a conductive material of which etching rate is lower than that of the photoelectric conversion layer 303 with respect to an etching gas (or an etchant) used for etching the photoelectric conversion layer 303. Additionally, a material for the protective electrode 218 is preferably a conductive material that does not react with the photoelectric conversion layer 303 to be an alloy. The other protective electrodes 245, 248, 246, and 247 are each also formed of a material and in a manufacturing process similar to those of the protective electrode 218.

For example, a conductive metal film (such as titanium (Ti) or molybdenum (Mo)) is formed, which is unlikely to be an alloy by being reacted with a photoelectric conversion layer (typically, amorphous silicon) which will be subsequently formed. Thereafter, a mask made of resist is formed and the conductive metal film is selectively etched so that the protective electrode 218 covering the wiring 284 is formed. Here, a Ti film with a thickness of 200 nm that can be obtained by a sputtering method is used. Note that the connection electrode 285, the terminal electrode 281, the source or drain electrodes 282 of the TFT 304, and the source or drain electrodes 283 of the TFT 305 are covered with the conductive metal film as well, and the protective electrodes 245, 248, 246, and 247 are formed. Thus, the conductive metal film covers also the side faces where the second-layer Al films of these electrodes are exposed; therefore, the conductive metal film can prevent an aluminum atom from dispersing into the photoelectric conversion layer.

Next, a photoelectric conversion layer 303 including a p-type semiconductor layer 303p, an i-type semiconductor layer 303i, and an n-type semiconductor layer 303n is formed over the third interlayer insulating film 217.

As for the p-type semiconductor layer 303p, an amorphous silicon film containing an impurity element belonging to Group 13, for example, boron (B) may be formed by a plasma CVD method.

Figure 11A:
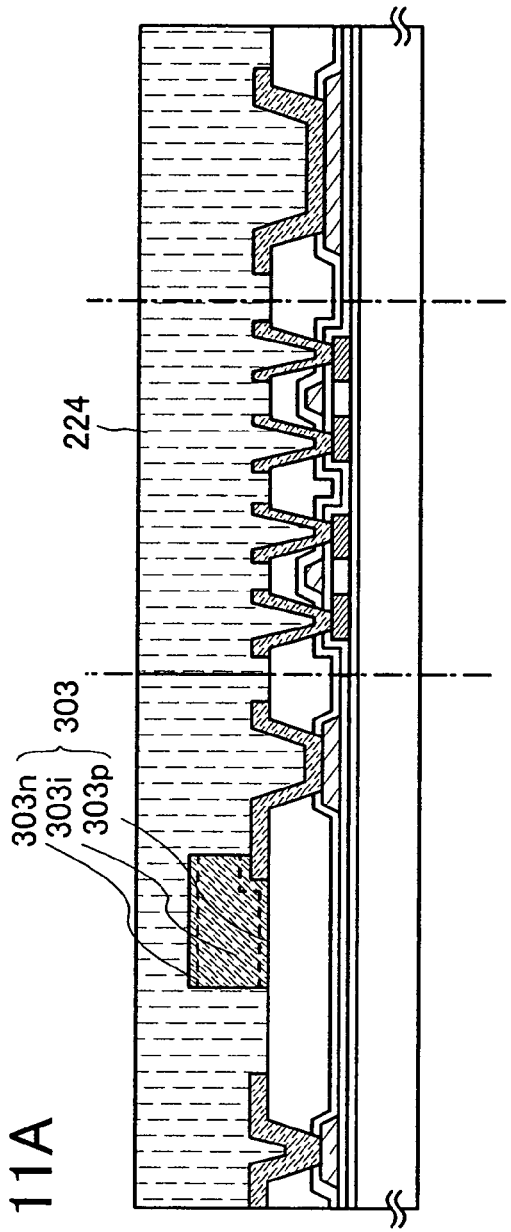
FIGS. 11A and 11B are diagrams showing a manufacturing process of a photo sensor of the present invention.

In FIG. 11A, the wiring 284 is in contact with the lowest layer of the photoelectric conversion layer 303, which is the p-type semiconductor layer 303p in this embodiment mode.

In the case of forming the protective electrodes, the wiring 284 and the protective electrode 218 are in contact with the lowest layer of the photoelectric conversion layer 303, in this embodiment mode, the p-type semiconductor layer 303p.

After the p-type semiconductor layer 303p is formed, further, the i-type semiconductor layer 303i and the n-type semiconductor layer 303n are sequentially formed. Accordingly, the photoelectric conversion layer 303 including the p-type semiconductor layer 303p, the i-type semiconductor layer 303i, and the n-type semiconductor layer 303n is formed.

As for the i-type semiconductor layer 303i, an amorphous silicon film may be formed by a plasma CVD method, for example. As for the n-type semiconductor layer 303n, an amorphous silicon film containing an impurity element belonging to Group 15, for example, phosphorus (P) may also be formed, or after an amorphous silicon film is formed, an impurity element belonging to Group 15 may also be introduced.

In addition, as for the p-type semiconductor layer 303p, the i-type semiconductor layer 303i, and the n-type semiconductor layer 303n, a semi-amorphous semiconductor film may also be used as well as the amorphous semiconductor film.

Next, a sealing layer 224 formed of an insulator material (for example, an inorganic insulating film containing silicon) is formed to have a thickness of 1 to 30 μm over the entire surface, and a state of FIG. 11A is obtained. Here, a silicon oxide film containing nitrogen with a thickness of 1 μm is formed by a CVD method as the insulator material film. The adhesiveness can be improved with the use of the insulating film formed by a CVD method.

Then, after the sealing layer 224 is etched to provide an opening, the terminal electrode 221 and the terminal electrode 222 are formed by a sputtering method. The terminal electrode 221 and the terminal electrode 222 are formed of a stacked-layer film of a titanium film (Ti film, 100 nm), a nickel film (Ni film, 300 nm), and a gold film (Au film, 50 nm). The fixing intensity of the terminal electrode 221 and the terminal electrode 222 obtained as described above is more than 5N, which is sufficient fixing intensity for a terminal electrode.

Figure 11B:
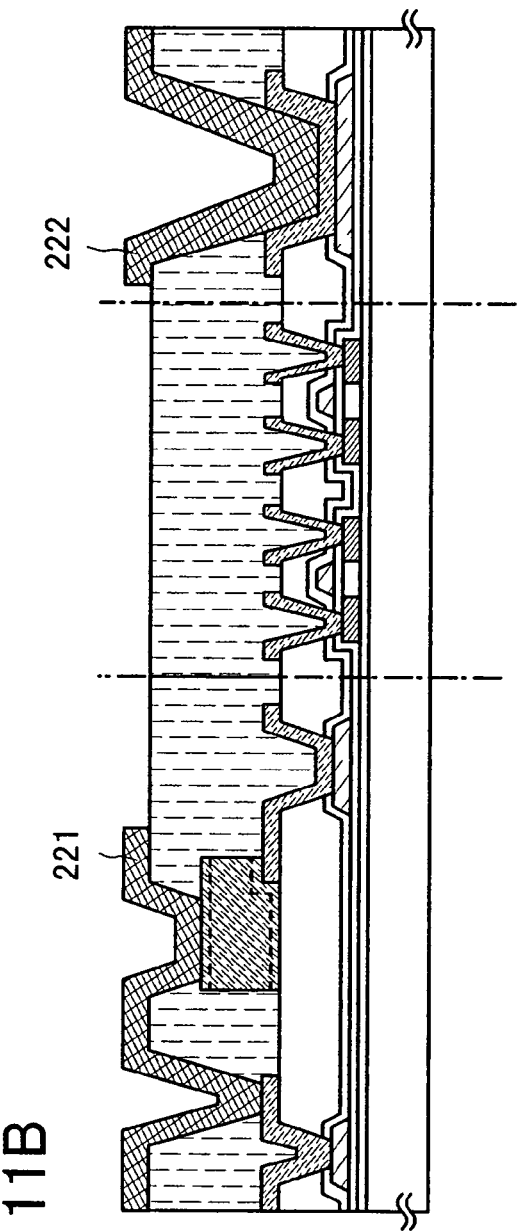

In the above steps, the terminal electrode 221 and the terminal electrode 222 that can be connected with solder are formed, and a structure shown in FIG. 11B is obtained.

Next, the obtained photo sensor is mounted on the mounting side of the substrate 260. The solder 264 and the solder 263 are used for connecting the terminal electrode 221 to the electrode 261, and the terminal electrode 222 to the electrode 262, respectively. The solder is formed in advance by a screen printing method or the like over the electrodes 261 and 262 of the substrate 260, and the solder and the terminal electrode are made in an abutted state to perform mounting by a reflow soldering treatment. The reflow soldering treatment is performed, for example, at a temperature of approximately 255 to 265° C. for about 10 seconds in an inert gas atmosphere. Moreover, as well as the solder, a bump formed of metal (such as gold or silver), a bump formed of a conductive resin, or the like can be used. Further, lead-free solder may also be used for mounting in consideration of an environmental problem.

As described above, it is possible to obtain a semiconductor device having a photoelectric conversion device including the photoelectric conversion layer 303, and the current mirror circuit 301.

Figure 6:
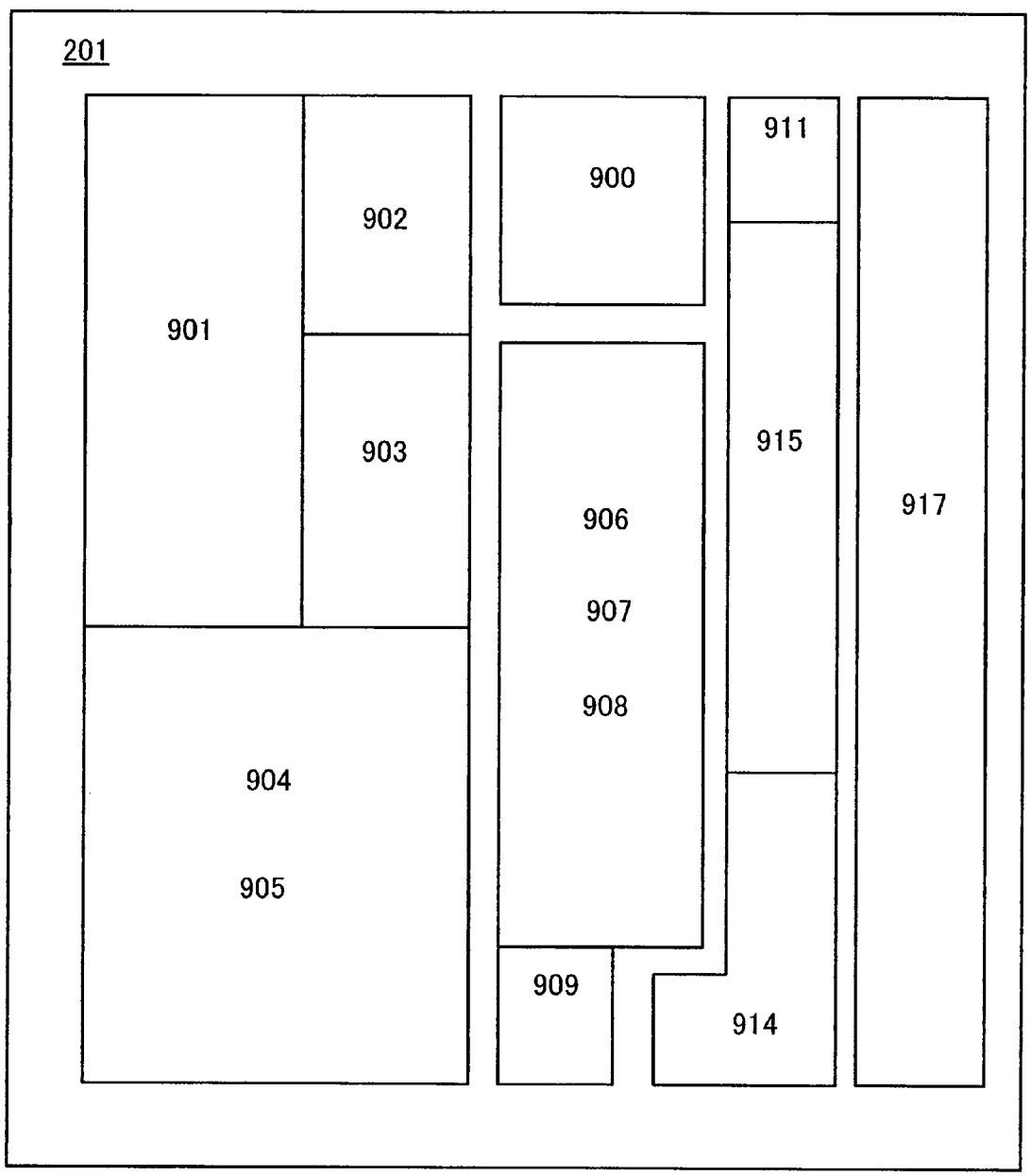
FIG. 6 is a block diagram showing a semiconductor device of the present invention capable of wireless communication.
Figure 12:
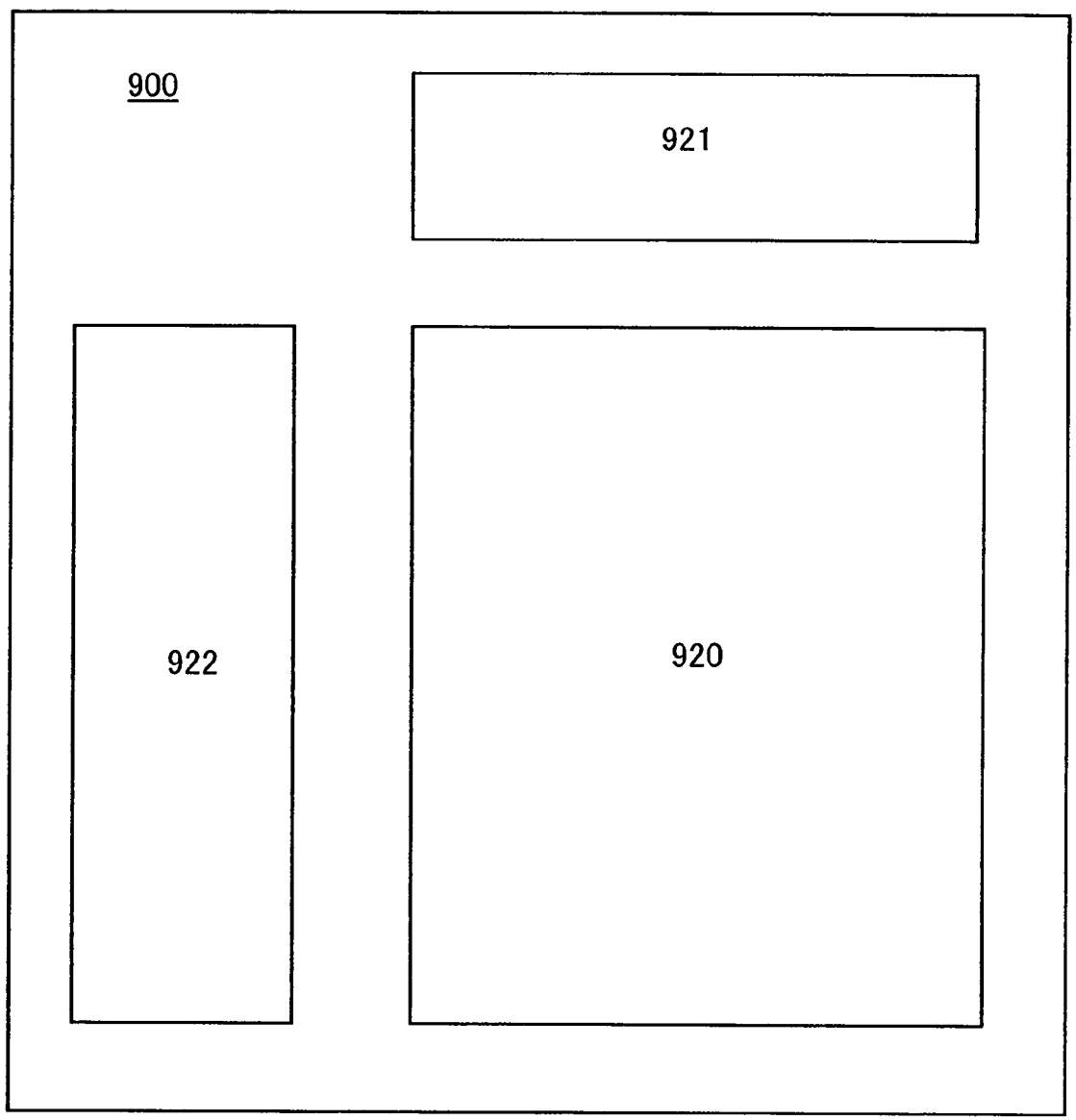
FIG. 12 is a block diagram showing a memory circuit of the present invention.
Figure 13:
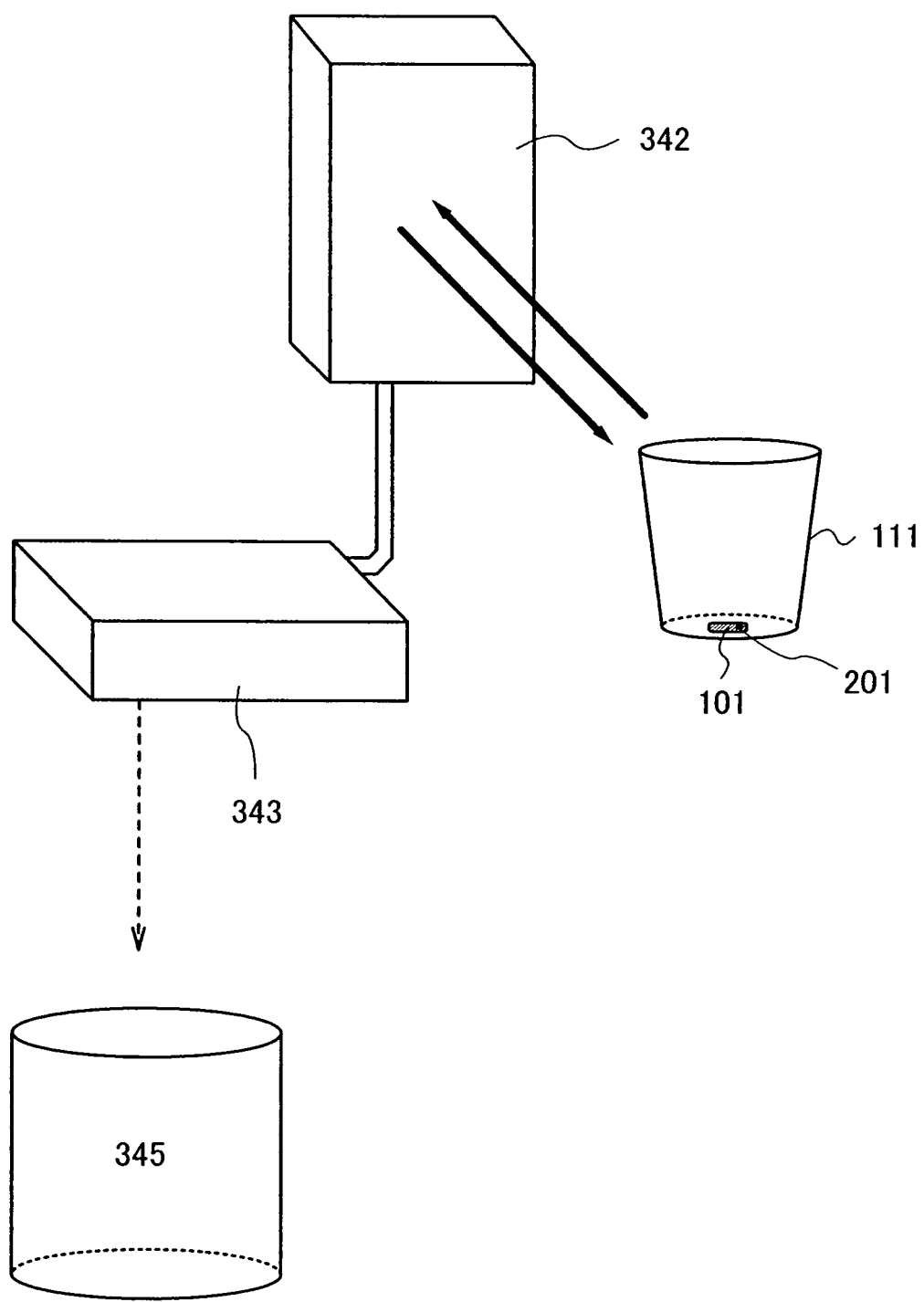
FIG. 13 is a diagram showing an examination system of the present invention.

Next, a structure and operation of the semiconductor device 201 of this embodiment mode capable of wireless communication is described with reference to FIGS. 6, 12, and 13.

First, the structure is described. As shown in FIG. 6, a semiconductor device (also referred to as an RFID, an ID chip, an IC chip, an IC tag, an ID tag, or a wireless chip) 201 of the present invention capable of wireless communication includes circuit blocks of an antenna 917, a high-frequency circuit 914, a power supply circuit 915, a reset circuit 911, a rectifier circuit 906, a demodulation circuit 907, an analog amplifier 908, a clock generation circuit 903, a modulation circuit 909, a signal output control circuit 901, a CRC (Cyclic Redundancy Code) circuit 902, and a memory circuit 900. The power supply circuit 915 includes circuit blocks of a rectifier circuit 913 and a storage capacitor 912. Further, as shown in FIG. 12, the memory circuit 900 includes a memory cell array 920, a column decoder 921, and a row decoder 922.

As the antenna 917, any of a dipole antenna, a patch antenna, a loop antenna, and a Yagi antenna can be used.

In addition, as a method for transmitting and receiving a wireless signal in the antenna 917, any of an electromagnetic coupling method, an electromagnetic induction method, and an electromagnetic wave method may be used.

Next, the operation of the semiconductor device 201 of the present invention capable of wireless communication is described. As shown in FIG. 13, a wireless signal is transmitted from an antenna unit 342 which is electrically connected to an interrogator (also referred to as a reader/writer) 343. The wireless signal includes an instruction from the interrogator (also referred to as a reader/writer) 343 to the semiconductor device 201 capable of wireless communication.

The wireless signal received by the antenna 917 is transmitted to each circuit block via the high-frequency circuit 914. The signal transmitted to the power supply circuit 915 via the high-frequency circuit 914 is input to the rectifier circuit 913.

Here, the rectifier circuit acts to rectify a polarity of the wireless signal. The signal is rectified and then smoothed by the storage capacitor. Then, a high power supply potential (VDD) is generated.

The wireless signal received by the antenna 917 is also transmitted to the rectifier circuit 906 via the high-frequency circuit 914. The signal is rectified and then demodulated by the demodulation circuit 907. The demodulated signal is amplified by the analog amplifier 908.

Further, the wireless signal received by the antenna 917 is also transmitted to the clock generation circuit 903 via the high-frequency circuit 914. The signal transmitted to the clock generation circuit 903 is frequency-divided to be a reference clock signal. Here, the reference clock signal is transmitted to each circuit block and used for latching a signal, selecting a signal, and the like.

The signal amplified by the analog amplifier 908 and the reference clock signal are transmitted to a code extraction circuit 904. In the code extraction circuit 904, an instruction transmitted from the interrogator 343 to the semiconductor device 201 capable of wireless communication is extracted from the signal amplified by the analog amplifier 908. The code extraction circuit 904 also forms a signal for controlling a code identification circuit 905.

The instruction extracted by the code extraction circuit 904 is transmitted to the code identification circuit 905. The code identification circuit 905 identifies the instruction transmitted from the interrogator 343. The code identification circuit 905 also has a role of controlling the CRC circuit 902, the memory circuit 900, and the signal output control circuit 901.

In this manner, the instruction transmitted from the interrogator (also referred to as a reader/writer) 343 is identified, and the CRC circuit 902, the memory circuit 900, and the signal output control circuit 901 are operated in accordance with the identified instruction. In addition, a signal including data which is stored in or written to the memory circuit 900, is output.

The memory circuit 900 includes data that is stored in advance, and data from the photo sensor 202 is written. The data that is stored in advance may be data or the like such as a serial number for examination or personal information of a patient. The data from the photo sensor 202 may be data of analytically processing change and degree of color of the reagent portion 108 that is described below.

The memory circuit 900 includes the memory cell array 920, the column decoder 921, and the row decoder 922.

The signal output control circuit 901 has a role of converting the signal including the data which is stored in or written to the memory circuit 900 into a signal encoded by an encoding method to which a standard of the ISO or the like is applied.

Lastly, in accordance with the encoded signal, the signal transmitted to the antenna 917 is modulated by the modulation circuit 909.

The modulated signal is received by the antenna unit 342 which is electrically connected to the interrogator 343. Then, the received signal is analyzed by the interrogator 343, and the data of the semiconductor device 201 of the present invention capable of wireless communication can be recognized.

In a wireless communication system using the semiconductor device 201 capable of wireless communication that uses an IC, formed using the present invention, the semiconductor device 201 capable of wireless communication, the interrogator 343 having a known structure, an antenna electrically connected to the interrogator, and a control terminal for controlling the interrogator can be used. A communication method of the semiconductor device 201 capable of wireless communication and the antenna electrically connected to the interrogator is one-way communication or two-way communication, and any of a space division multiplexing method, a polarization division multiplexing method, a frequency-division multiplexing method, a time-division multiplexing method, a code division multiplexing method, and an orthogonal frequency division multiplexing method can also be used.

The wireless signal is a signal in which a carrier wave is modulated. Modulation of a carrier wave is an analog modulation or a digital modulation, which may be any of an amplitude modulation, a phase modulation, a frequency modulation, and spread spectrum.

As for a frequency of a carrier wave, any of the following can be employed: a submillimeter wave of greater than or equal to 300 GHz and less than or equal to 3 THz; an extra high frequency of greater than or equal to 30 GHz and less than 300 GHz; a super high frequency of greater than or equal to 3 GHz and less than 30 GHz; an ultra high frequency of greater than or equal to 300 MHz and less than 3 GHz; a very high frequency of greater than or equal to 30 MHz and less than 300 MHz; a high frequency of greater than or equal to 3 MHz and less than 30 MHz; a medium frequency of greater than or equal to 300 kHz and less than 3 MHz; a low frequency of greater than or equal to 30 kHz and less than 300 kHz; and a very low frequency of greater than or equal to 3 kHz and less than 30 kHz.

Also, as shown in FIGS. 2B and 3B, the chip 105 of this embodiment mode may include the battery 204. The battery used in this embodiment mode is described below with reference to FIGS. 14 to 20.

In this specification, a battery that includes an antenna; a circuit that charges the battery with electromotive force that is generated by an electromagnetic wave received by the antenna; and a medium that charges the electromotive force is also called an RF battery or a wireless battery.

Also, in this specification, a battery refers to a secondary battery or an accumulator battery, and refers to a device that changes electrical energy obtained from an external power supply into chemical energy and stores the energy, and takes it out again as power as necessary. In addition, a capacitor refers to a device in which two conductors that are insulated are near each other and one of the two conductors takes on a positive charge and the other takes on a negative charge, and charge is store by an attracting force between electricity thereof.

Note that "battery" in this specification means a secondary battery whose continuous operating time can be restored by charging. Further, as a battery, a battery formed in a sheet-like form with a thin thickness or a battery formed in a cylindrical shape with a small diameter is preferably used although the type of the battery may differ depending on the intended use of the battery. For example, by using a lithium battery, preferably a lithium polymer battery that uses a gel electrolyte, a lithium ion battery, or the like, miniaturization is possible. Needless to say, any battery may be used as long as it is chargeable. For example, the following batteries that are chargeable and dischargeable can be used: a nickel metal hydride battery, a nickel cadmium-battery, an organic radical battery, a lead-acid battery, an air secondary battery, a nickel-zinc battery, a silver-zinc battery, or the like. Alternatively, a high-capacity capacitor or the like may be used.

Note that as a high-capacity capacitor that can be used as a battery of this embodiment mode it is preferable to use a capacitor having electrodes whose opposed areas are large. In particular, it is preferable to use an electric double layer capacitor which is formed using an electrode material having a large specific surface area such as activated carbon, fullerene, or a carbon nanotube. A capacitor has a simpler structure than a battery and can be easily formed to be thin and formed by stacking layers. An electric double layer capacitor has a function of storing electric power and does not deteriorate much even after it is charged and discharged a number of times. Further, the electric double layer capacitor has an excellent property that it can be charged rapidly.

Figure 14:
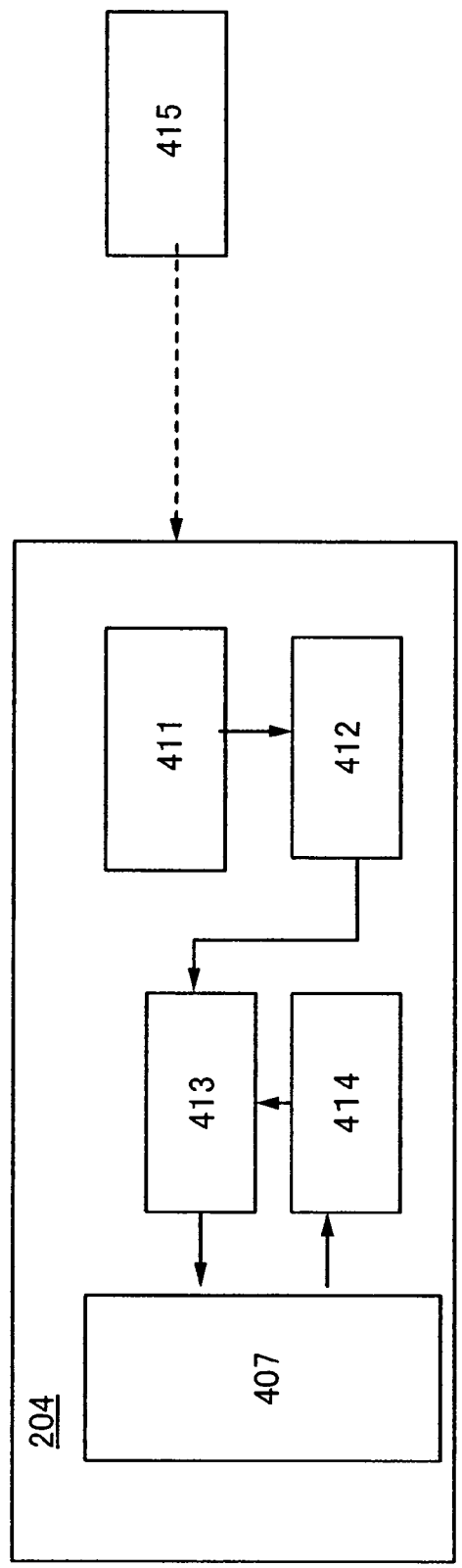
FIG. 14 is a block diagram showing a battery of the present invention.

In FIG. 14, an internal antenna circuit 411 receives a wireless signal generated by an external antenna circuit 415. The signal received by the internal antenna circuit 411 is input to a rectifier circuit 412 to be converted into a direct current. A charge circuit 413 generates current based on power from the rectifier circuit 412, and charges a battery 407. A charge control circuit 414 monitors so that the battery 407 is not overcharged, and controls the charge circuit 413 when an amount of charge increases in order to suppress the amount of charge. Note that the charge circuit 413 can be composed of, for example, a voltage control circuit (also called a "regulator") and a switch circuit. Note that by having a diode as the switch circuit, the charge control circuit does not have to be provided. In addition, the voltage control circuit may be a voltage and current control circuit or a constant current source circuit.

Figure 15A:
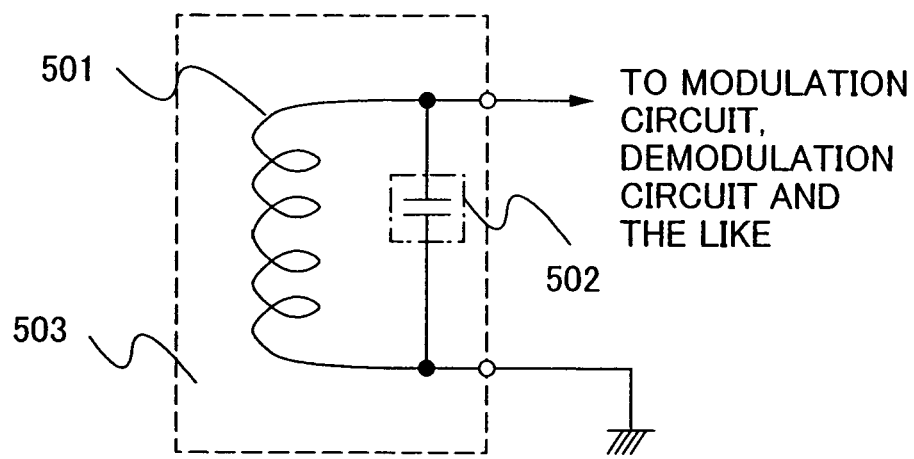
FIGS. 15A and 15B are diagrams showing circuits included in a battery of the present invention.
Figure 15B:
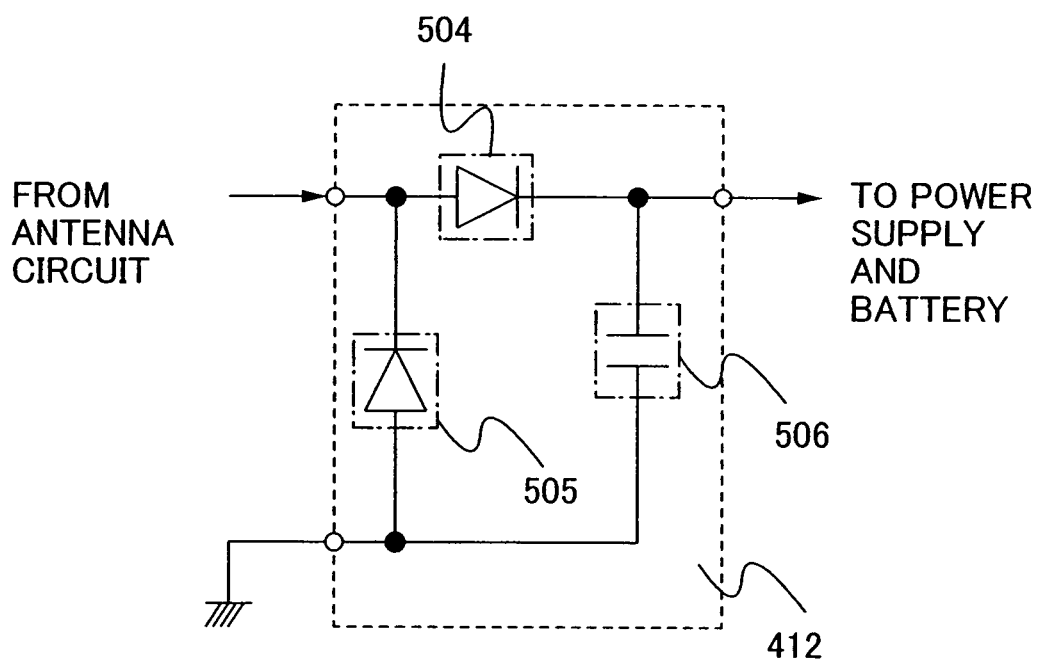

Note that as the internal antenna circuit 411 and the external antenna circuit 415, the antenna 501 and the antenna circuit 503 composed of a resonant capacitor 502 shown in FIG. 15A can be used, respectively, for example. Further, it is acceptable as long as the rectifier circuit 412 is a circuit that converts an alternate current signal induced by electromagnetic waves received by the internal antenna circuit 411 and the external antenna circuit 415, into a direct current signal. For example, as shown in FIG. 15B, the rectifier circuit 412 can be composed of a diode 504, a diode 505, and a smoothing capacitor 506.

In this embodiment mode, a frequency of a wireless signal received by the internal antenna circuit 411 may be, for example, 125 kHz, 13.56 MHz, 915 MHz, 2.45 GHz, or the like. However, the frequency of the signal received by the internal antenna circuit is not limited to those, and for example, any of the following can be employed: a submillimeter wave of greater than or equal to 300 GHz and less than or equal to 3 THz; an extra high frequency of greater than or equal to 30 GHz and less than 300 GHz; a super high frequency of greater than or equal to 3 GHz and less than 30 GHz; an ultra high frequency of greater than or equal to 300 MHz and less than 3 GHz; a very high frequency of greater than or equal to 30 MHz and less than 300 MHz; a high frequency of greater than or equal to 3 MHz and less than 30 MHz; a medium frequency of greater than or equal to 300 KHz and less than 3 MHz; a low frequency of greater than or equal to 30 KHz and less than 300 KHz; and a very low frequency of greater than or equal to 3 KHz and less than 30 KHz.

Further, a signal transmitted or received between the internal antenna circuit 411 and the external antenna circuit 415 is a modulated carrier wave. As a method of modulating the carrier wave, analog modulation or digital modulation may be used. Amplitude modulation, phase modulation, frequency modulation, or spread spectrum may also be used. Preferably, amplitude modulation or frequency modulation is used. For example, as the wireless signal, electric waves that are unintentionally received from the outside such as electric waves of relay stations of cellular phones (e.g., 800 to 900 MHz, 1.5 GHz, or 1.9 to 2.1 GHz), electric waves emitted from cellular phones, electric waves of wave clocks (e.g., 40 kHz), noise of a household AC power supply (e.g., 60 Hz), or the like can also be utilized. Further, by provision of a plurality of antenna circuits each of which uses an antenna with different length and shape as the internal antenna circuit 411, various wireless signals can be utilized for charging the battery 407.

The length and shape of the antenna provided in the internal antenna circuit 411 and the external antenna circuit 415 are decided so as to easily receive these wireless signals. Further, in the case of receiving a plurality of these electric waves, it is preferable to provide a plurality of antenna circuits each of which includes an antenna with different length and shape.

The shape of the antenna provided in the internal antenna circuit 411 or the external antenna circuit 415 is not particularly limited. That is, as a transmission system of a signal that is applied to the internal antenna circuit 411 or the external antenna circuit 415, an electromagnetic coupling system, an electromagnetic induction system, a micro-wave system, or the like can be used. The transmission system may be selected appropriately by a practitioner in consideration of usage, and an antenna having an optimal length and shape may be provided in accordance with the transmission system.

In the case of employing, for example, an electromagnetic coupling system or an electromagnetic induction system (e.g., 13.56 MHz band) as the transmission system, electromagnetic induction caused by a change in electric field density is used. Therefore, the conductive film which functions as an antenna is formed in an annular shape (e.g., a loop antenna) or a spiral shape (e.g., a spiral antenna or a helical antenna).

A micro-wave system (e.g., UHF band (860 to 960 MHz band), a 2.45 GHz band, or the like) can be used as the transmission system. In that case, the length and shape of the conductive film which functions as an antenna may be appropriately set in consideration of the wavelength of an electric wave used for signal transmission. For example, a conductive film which functions as an antenna can be formed in a linear shape (e.g., a dipole antenna), a flat shape (e.g., a patch antenna), or the like. The shape of the conductive film which functions as the antenna is not limited to a linear shape, and a curved-line shape, a meander shape, or a combination thereof may be employed in consideration of the wavelength of an electromagnetic wave.

Figure 16A:
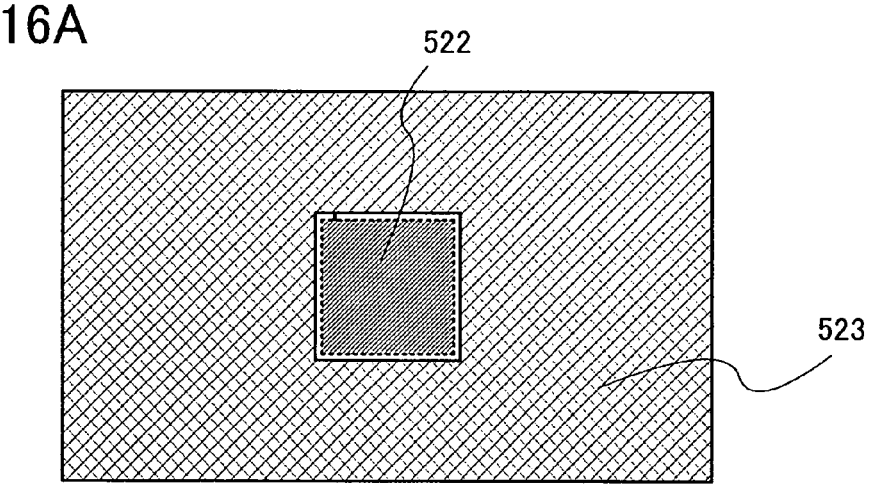
FIGS. 16A to 16E are top views of circuits included in a battery of the present invention.

Here, examples of the shape of the antenna provided in the internal antenna circuit 411 or the external antenna circuit 415 are shown in FIGS. 16A to 16E. For example, as shown in FIG. 16A, a structure in which an antenna 523, which is sheet-shaped, is provided around a circuit element 522 over which a variety of circuits or the like is provided may be used. Note that the circuit element 522 refers to each element of the semiconductor device 201 capable of wireless communication from which the internal antenna circuit 411 or the external antenna circuit 415 is removed.

Figure 16B:
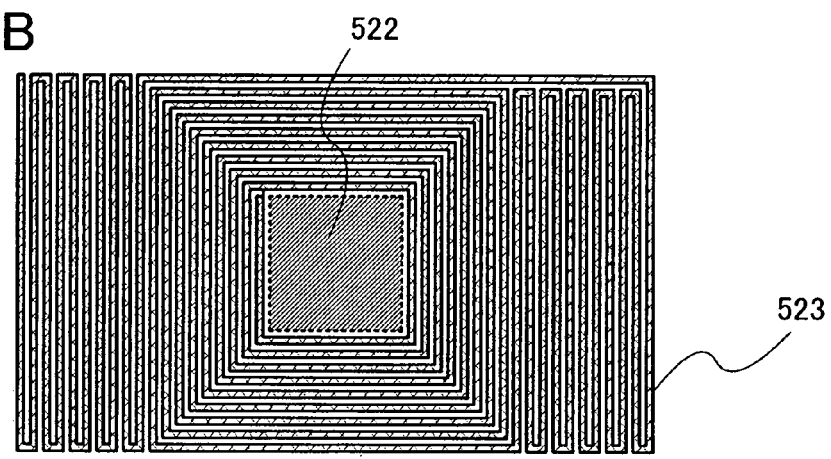
Figure 16C:
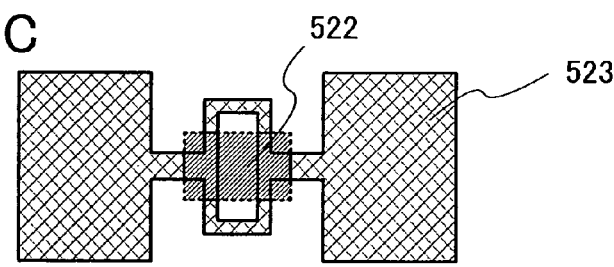
Figure 16D:
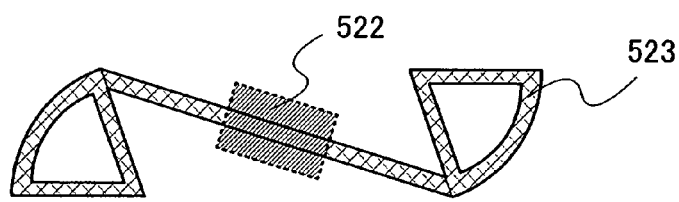
Figure 16E:
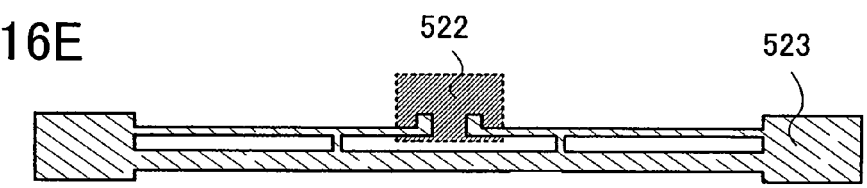

In addition, as shown in FIG. 16B, a structure in which the antenna 523, which is thin, is provided around the circuit element 522 over which a variety of circuits or the like are provided may be used. Further, as shown in FIG. 16C, the shape of the antenna 523 for receiving a high frequency electromagnetic wave may be used and provided for the circuit element 522 over which a variety of circuits or the like are provided. In addition, as shown in FIG. 16D, the antenna 523, which is 180 degree omnidirectional (capable of receiving signals equally from any direction), may be provided for the circuit element 522 over which a variety of circuits or the like are provided. In addition, as shown in FIG. 16E, the antenna 523 which is extended to have a stick shape may be provided for the circuit element 522 over which a variety of circuits or the like are provided. The internal antenna circuit 411 or the external antenna circuit 415 can be formed by a combination of antennas with these shapes.

In FIGS. 16A to 16E, there is no particular limitation on the connection between the circuit element 522 over which a variety of circuits or the like are provided and the antenna. For example, the antenna 523 and the circuit element 522 over which circuits or the like are provided may be connected by wire bonding or bump bonding. Alternatively, an electrode formed in a portion of the circuit element 522 over which circuits or the like are provided may be attached to the antenna 523; in this method, an ACF (anisotropic conductive film) can be used for attaching the circuit element 522 to the antenna 523. An appropriate length of the antenna 523 varies depending on a frequency for receiving signals. Therefore, the length is generally a fraction of a whole number of the wavelength, for example, when the frequency is 2.45 GHz, the length of the antenna may be about 60 mm (a half wavelength), or about 30 mm (a quarter wavelength).

Figure 17:
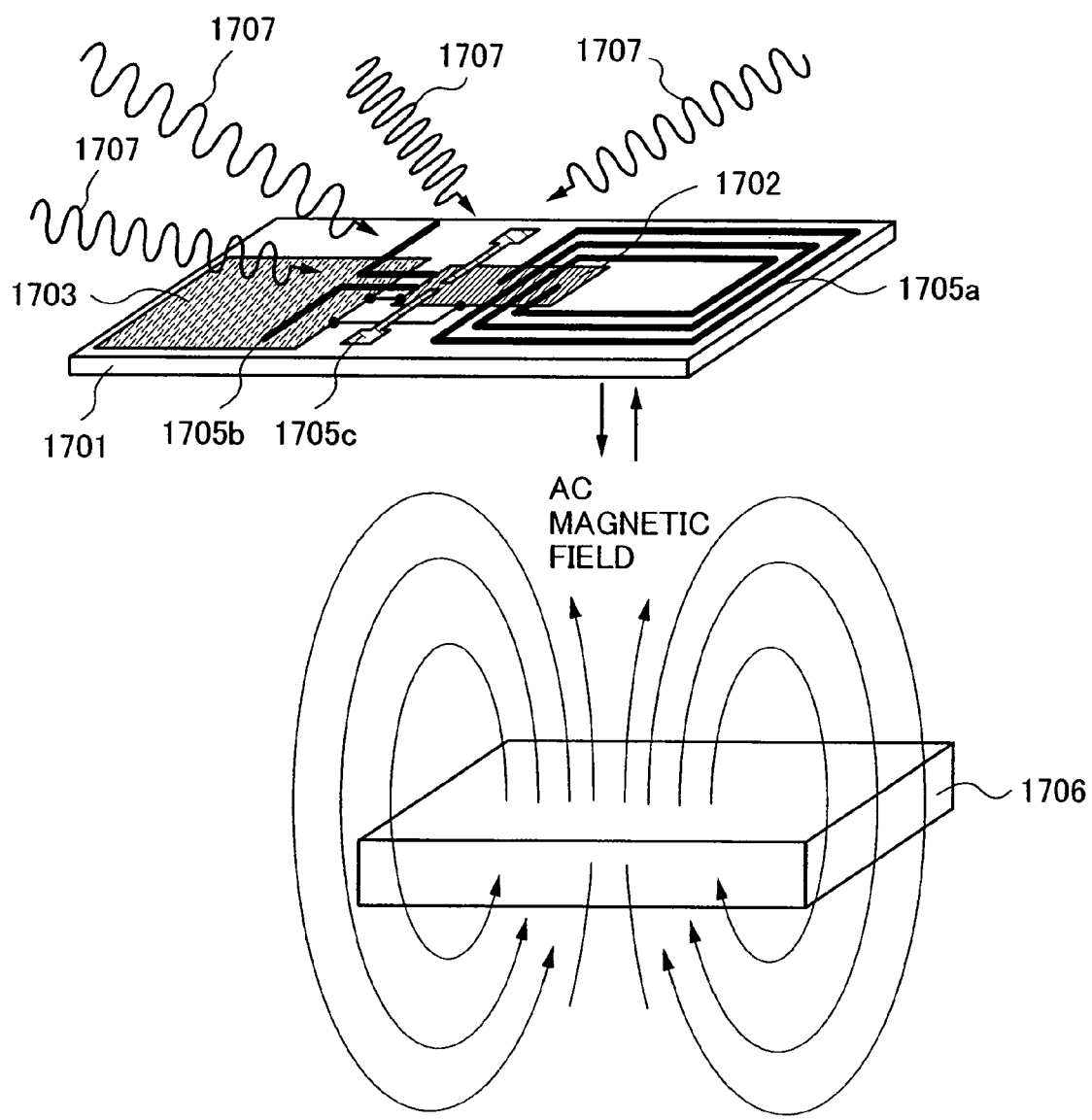
FIG. 17 is a diagram showing a circuit included in a battery of the present invention.

The internal antenna circuit 411 may have a multiband antenna structure, by which electromagnetic waves in a plurality of frequency bands can be received. For example, as shown in FIG. 17, the internal antenna circuit may be formed of a plurality of antenna circuits. In the structure shown in FIG. 17, a first antenna circuit 1705a, a second antenna circuit 1705b, a third antenna circuit 1705c, a circuit element 1702 including a control circuit, and a battery 1703 are provided over a substrate 1701. Note that the first antenna circuit 1705a, the second antenna circuit 1705b, and the third antenna circuit 1705c are electrically connected to the control circuit provided in the circuit element 1702. Reference numeral 1706 denotes a transmitter which transmits an electromagnetic wave for charging the battery and is provided in a display portion or the like.

The electric waves received by the first antenna circuit 1705a, the second antenna circuit 1705b, and the third antenna circuit 1705c are input to the battery 1703 through a rectification circuit in the control circuit formed in the circuit element 1702, thereby charging the battery 1703.

Here, an example where the electric wave transmitted from the transmitter 1706 is received by the first antenna circuit 1705a and an external wireless signal 1707 is received by the second antenna circuit 1705b and the third antenna circuit 1705c is shown. Further, a relation of connection among the first antenna circuit 1705a, the second antenna circuit 1705b, and the third antenna circuit 1705c is not particularly limited. For example, all antennas may be electrically connected, or alternatively antennas may be provided independently without being electrically connected to each other.

The lengths and shapes of the first antenna circuit 1705a, the second antenna circuit 1705b, and the third antenna circuit 1705c used for charging the battery 1703 are not limited to those shown in FIG. 17. Here, an example is shown, in which linear antennas having different lengths (dipole antennas) are provided as antennas of the second antenna circuit 1705b and the third antenna circuit 1705c. Alternatively, for example, a combination of a dipole antenna and a coiled antenna or a combination of a dipole antenna and a patch antenna may be used. Thus, a plurality of antennas having different lengths and shapes can be provided as the antennas used for charging the battery 1703, whereby various wireless signals can be received. Accordingly, charging efficiency can be improved. In particular, when a combination of antennas having different shapes such as a combination of a patch antenna and a dipole antenna is provided (for example, a folded dipole antenna is provided around a patch antenna), it becomes possible to utilize a limited space efficiently. The example of providing three antenna circuits of the first antenna circuit 1705a, the second antenna circuit 1705b, and the third antenna circuit 1705c in the electronic pen is shown in this embodiment mode; however, the present invention is not limited to this. A structure where one antenna circuit, or three or more antenna circuits is/are provided may be employed.

For example, the frequency of signals transmitted and received between the first antenna circuit 1705a and the transmitter 1706 may be 125 kHz, 13.56 MHz, 915 MHz, 2.45 GHz, or the like, to each of which a standard of the ISO is applied. However, the frequency of the signals transmitted and received between the first antenna circuit 1705a and the transmitter 1706 is not limited to this, and for example, any of the following can be employed: a submillimeter wave of greater than or equal to 300 GHz and less than or equal to 3 THz; an extra high frequency of greater than or equal to 30 GHz and less than 300 GHz; a super high frequency of greater than or equal to 3 GHz and less than 30 GHz; an ultra high frequency of greater than or equal to 300 MHz and less than 3 GHz; a very high frequency of greater than or equal to 30 MHz and less than 300 MHz; a high frequency of greater than or equal to 3 MHz and less than 30 MHz; a medium frequency of greater than or equal to 300 KHz and less than 3 MHz; a low frequency of greater than or equal to 30 KHz and less than 300 KHz; and a very low frequency of greater than or equal to 3 KHz and less than 30 KHz. The signal transmitted and received between the first antenna circuit 1705a and the transmitter 1706 is a modulated carrier wave. As a method of modulating the carrier wave, analog modulation or digital modulation may be used: amplitude modulation, phase modulation, frequency modulation, or spread spectrum may also be used. Preferably, amplitude modulation or frequency modulation is used.

As the external wireless signal 1707 received by the antennas of the second antenna circuit 1705b and the third antenna circuit 1705c, electric waves of relay stations of cellular phones (e.g., 800 to 900 MHz, 1.5 GHz, or 1.9 to 2.1 GHz), electric waves emitted from cellular phones, electric waves of wave clocks (e.g., 40 kHz), noise of a household AC power supply (e.g., 60 Hz), electric waves generated unintentionally from other readers/writers, or the like can also be utilized. When the battery is charged wirelessly by reception of external wireless signals, a battery charger or the like for charging the battery is not needed additionally; accordingly, the electronic pen can be manufactured at reduced cost. Further, by provision of a plurality of antenna circuits each of which uses an antenna with different length and shape as shown in FIG. 17, various wireless signals can be utilized for charging the battery 1703. The lengths and shapes of the antennas provided in the second antenna circuit 1705b and the third antenna circuit 1705c are preferably decided so as to easily receive these wireless signals. Further, the mode where the first antenna circuit receives the electromagnetic wave from the transmitter 1706 is used in FIG. 17; however, the present invention is not limited to this and a mode where all antenna circuits receive external wireless signals for charging the battery may be employed.

The example of providing the plurality of antenna circuits 1705a, 1705b, and 1705c, the circuit element 1702, and the battery 1703 over the one substrate 1701 is shown in FIG. 17; however, the present invention is not limited to the structure shown in FIG. 17, and each of them may be provided over separate substrates.

Next, a structural example of a thin-film battery is described as the battery 407 shown in FIG. 14. In this embodiment mode, a structural example of a battery in the case of using a lithium ion battery is shown in FIG. 18.

Figure 18:
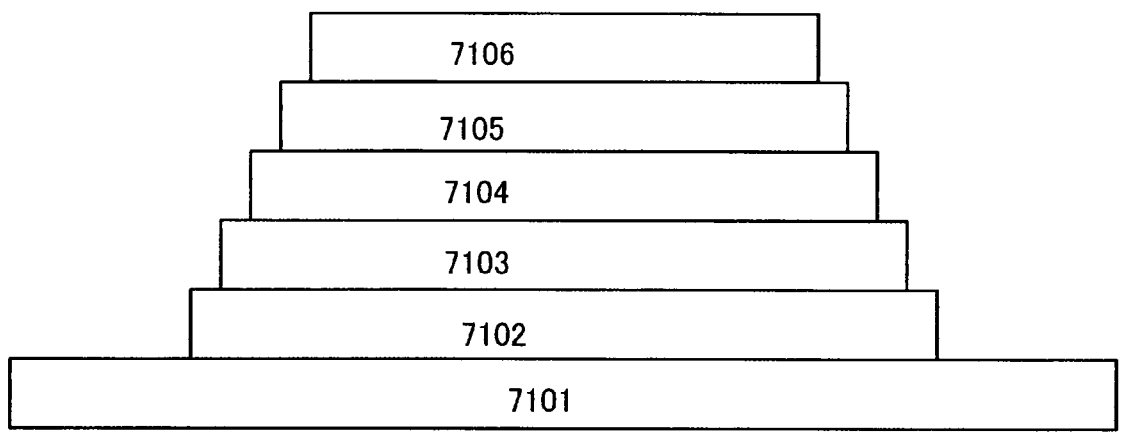
FIG. 18 is a cross-sectional diagram of a battery of the present invention.

FIG. 18 is a cross-sectional schematic view of a thin-film battery. A current-collecting thin film 7102 to serve as an electrode is formed over a substrate 7101. The current-collecting thin film 7102 is required to have high adhesion to a negative electrode active material layer 7103 and also have low resistance. For example, aluminum, copper, nickel, vanadium, or the like can be used. Next, the negative electrode active material layer 7103 is formed over the current-collecting thin film 7102. Generally, vanadium oxide ($V_2O_5$) or the like is used. Next, a solid electrolyte layer 7104 is formed over the negative electrode active material layer 7103. Generally, lithium phosphate ($Li_3PO_4$) or the like is used. Then, a positive electrode active material layer 7105 is formed over the solid electrolyte layer 7104. Generally, lithium manganate ($LiMn_2O_4$) or the like is used. Lithium cobaltate ($LiCoO_2$) or lithium nickel oxide ($LiNiO_2$) can also be used. Next, a current-collecting thin film 7106 to serve as an electrode is formed over the positive electrode active material layer 7105. The current-collecting thin film 7106 is required to have high adhesion to the positive electrode active material layer 7105 and also have low resistance. For example, aluminum, copper, nickel, vanadium, or the like can be used. Note that compared to a nickel-cadmium battery, a lead-acid battery, or the like, the lithium ion battery causes less memory effect and have a larger amount of current.

Each of the above thin layers of the current-collecting thin film 7102, the negative electrode active material layer 7103, the solid electrolyte layer 7104, the positive electrode active material layer 7105, and the current-collecting thin film 7106 may be formed by using a sputtering technique or a vapor-deposition technique. In addition, each thickness of the current-collecting thin film 7102, the negative electrode active material layer 7103, the solid electrolyte layer 7104, the positive electrode active material layer 7105, and the current-collecting thin film 7106 is preferably 0.1 to 3 μm.

Next, the operation in charging and discharging the battery will be described. In charging the battery, lithium ions are desorbed from a positive electrode active material. Then, the lithium ions are absorbed into a negative electrode active material through the solid electrolyte layer. At this time, electrons are released to the outside from the positive electrode active material.

In discharging the battery, on the other hand, lithium ions are desorbed from the negative electrode active material. Then, the lithium ions are absorbed into the positive electrode active material through the solid electrolyte layer. At this time, electrons are released to the outside from the negative electrode active material layer. The thin-film secondary battery operates in this manner.

Note that it is preferable to stack another set of thin layers of the current-collecting thin film 7102, the negative electrode active material layer 7103, the solid electrolyte layer 7104, the positive electrode active material layer 7105, and the current-collecting thin film 7106, because larger electric power can be charged in or discharged from the battery with such a structure.

The battery in this embodiment mode is a thin film with a thickness of about 10 μm or less and capable of charging and discharging. Therefore, when the battery of this embodiment mode is used, a small and light-weight examination element can be manufactured.

When using a chargeable battery, it is generally necessary to control charging and discharging of the battery. It is necessary to conduct charging while monitoring the charge state of a battery in order to prevent overcharging. A circuit for charge control will be described in this embodiment mode.

Figure 19:
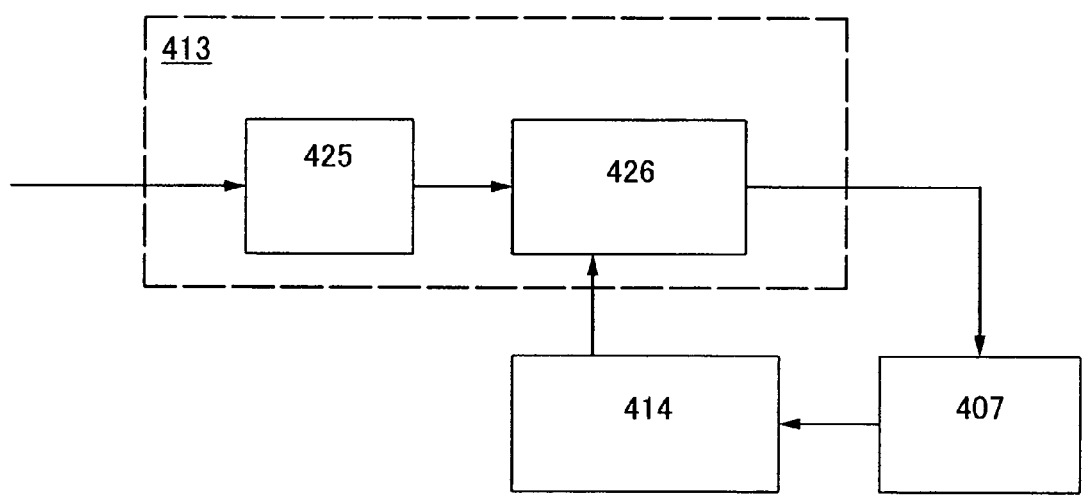
FIG. 19 is a block diagram showing a circuit included in a battery of the present invention.

FIG. 19 is a block diagram of the charge circuit 413, the charge control circuit 414, and the battery 407 shown in FIG. 14.

In the example shown in FIG. 19, the charge circuit 413 includes a constant current source circuit 425 and a switch circuit 426, and is connected to the charge control circuit 414 and the battery 407. The charge circuit shown in FIG. 19 is only an example, and the invention is not limited to this structure. A different structure may be employed. Although the battery 407 is charged with a constant current in this embodiment mode, a power supply may be switched from a constant current at a certain point so that the battery can be charged with a constant voltage. In addition, another method without using a constant current may also be employed. Further, transistors included in the circuits which will be described below may be any of thin film transistors, transistors on a single-crystalline substrate, or organic transistors.

Figure 20:
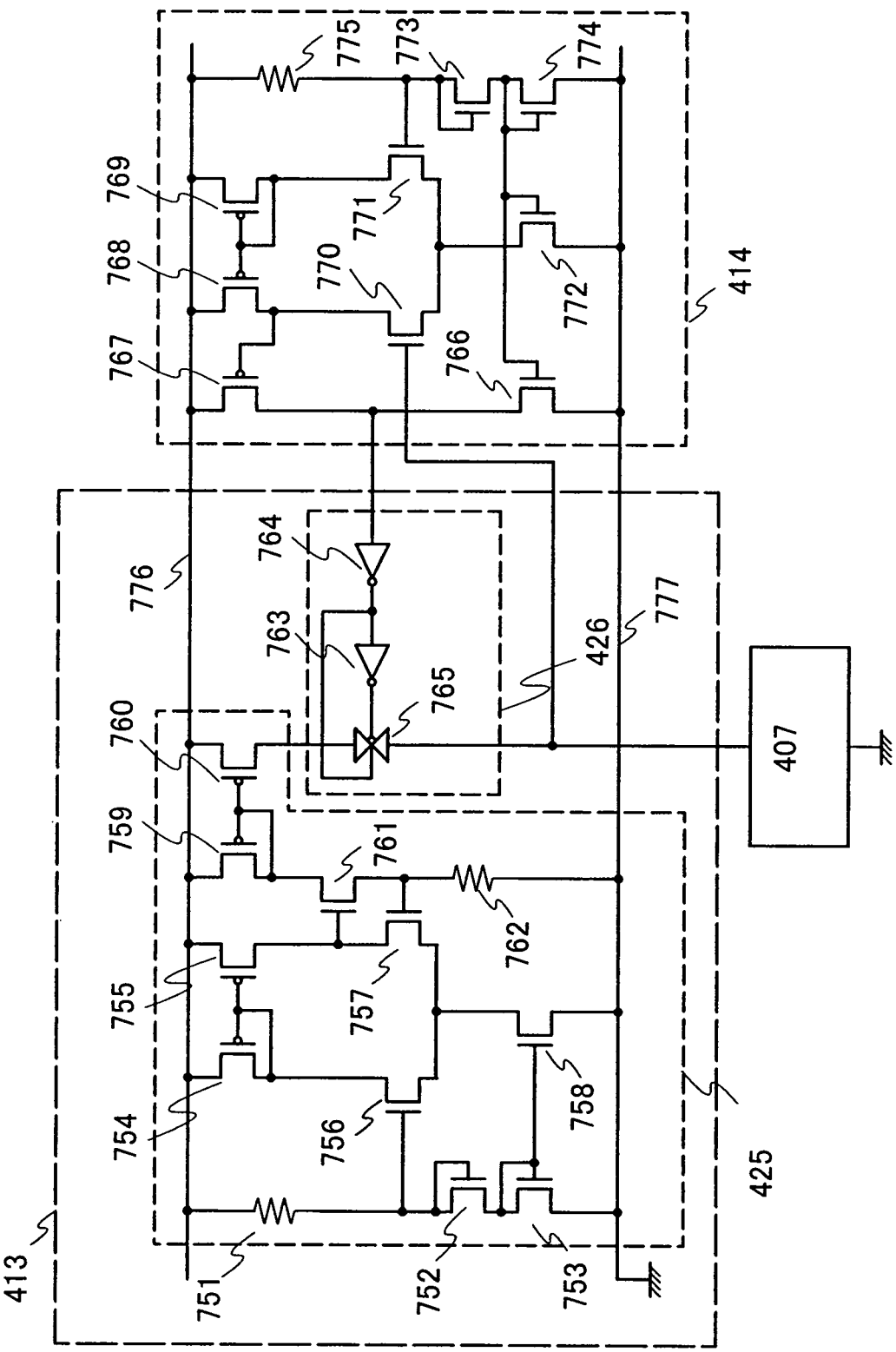
FIG. 20 is a circuit diagram included in a battery of the present invention.

FIG. 20 is a detailed diagram of the circuit shown in FIG. 19. The operation of the circuit will be described below. The constant current source circuit 425, the switch circuit 426, and the charge control circuit 414 use a high potential power supply line 776 and a low potential power supply line 777 as power supply lines. In FIG. 19, the low potential power supply line 777 is used as a GND line. However, the potential of the low potential power supply line 777 is not limited to the GND, and may have a different potential.

The constant current source circuit 425 includes transistors 752 to 761 and resistors 751 and 762. A current flows into the transistors 752 and 753 from the high potential power supply line 776 through the resistor 751, so that the transistors 752 and 753 are turned ON.

The transistors 754, 755, 756, 757, and 758 constitute a feedback differential amplifier, and the gate potential of the transistor 757 is almost the same as the gate potential of the transistor 752. The drain current of the transistor 761 has a value obtained by dividing a potential difference between the gate potential of the transistor 757 and the potential of the low potential power supply line 777 by the resistance value of the resistor 762. The drain current is input into the current mirror circuit which is constructed from the transistors 759 and 760, and an output current of the current mirror circuit is supplied to the switch circuit 426. The constant current source circuit 425 is not limited to this structure and a different structure may be used.

The switch circuit 426 includes a transmission gate 765 and inverters 763 and 764. The input signal of the inverter 764 controls whether to supply a current to the battery 407 from the constant current source circuit 425. The switch circuit is not limited to this structure and a different structure may be used.

The charge control circuit 414 includes transistors 766 to 774 and a resistor 775. A current flows into the transistors 773 and 774 from the high potential power supply line 776 through the resistor 775, so that the transistors 773 and 774 are turned ON. The transistors 768, 769, 770, 771, and 772 constitute a differential comparator. When the gate potential of the transistor 770 is lower than the gate potential of the transistor 771, the drain potential of the transistor 768 has almost the same value as the potential of the high potential power supply line 776, whereas when the gate potential of the transistor 770 is higher than the gate potential of the transistor 771, the drain potential of the transistor 768 has almost the same value as the source potential of the transistor 770.

When the drain potential of the transistor 768 has almost the same value as the potential of the high potential power supply line, the charge amount control circuit outputs a low-level potential through a buffer which is constituted from the transistors 767 and 766. When the drain potential of the transistor 768 has almost the same value as the source potential of the transistor 770, the charge amount control circuit outputs a high-level potential through the buffer which is constituted from the transistors 767 and 766.

When the output of the charge control circuit 414 is low, a current is supplied to the battery 407 through the switch circuit 426. Meanwhile, when the output of the charge control circuit 414 is high, the switch circuit 426 is turned OFF and no current is supplied to the battery 407. A gate of the transistor 770 is connected to the battery 407; therefore, when the battery 407 is charged and the potential of the battery surpasses the threshold voltage of the comparator of the charge control circuit 414, charging is stopped. Although the threshold voltage of the comparator in this embodiment mode is set at the gate potential of the transistor 773, the potential is not limited to this value, and a different potential may be set. The set potential is generally determined in accordance with the intended use of the device and the performance of the battery. The structure of the charge circuit for the battery is not limited to this structure.

Figure 1B:
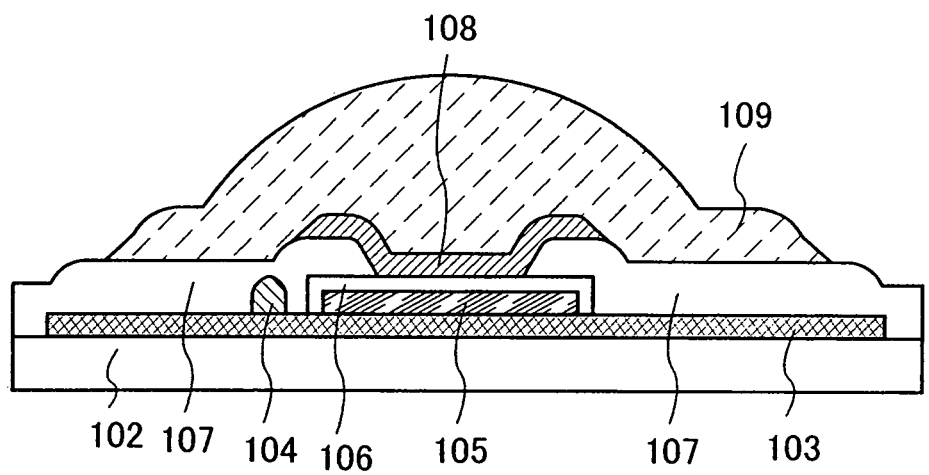

The photo sensor 202, the semiconductor device 201 capable of wireless communication, and the battery 204 formed in the chip 105 shown in FIG. 1B are formed in the foregoing manner.

As shown in FIG. 1B, when the hygroscopic portion 109 is dipped in urine, the urine reaches the reagent portion 108. Thereafter, the LED 104 or the LED 203 is made to emit light, a change in color or the colored degree of the reagent portion 108 is detected by the photo sensor 202 and stored in the semiconductor device 201 capable of wireless communication, and an analysis process is performed in a circuit mounted to the semiconductor device 201 capable of wireless communication. Subsequently, examination data that is analytically processed is transmitted to an external database 345 or the like via the interrogator 343 by the antenna 103. Then, the examination data is stored in the database 345.

The antenna 103 may be electrically connected to each of the antenna 917, the internal antenna circuit 411, and the external antenna circuit 415. Alternatively, the antenna 103 may double as any one or a plurality of the antenna 917, the internal antenna circuit 411, and the external antenna circuit 415.

The examination element 101 of this embodiment mode is attached to an inside (a side portion or a bottom portion) of a paper cup for urinalysis, as described above. Accordingly, chip size is not limited as long as it is within a range that does not exceed the size of the cup.

In addition, the examination element 101 can be reused by providing an attachment portion around the reagent portion 108 and the hygroscopic portion 109 to make them detachable.

This application is based on Japanese Patent Application serial no. 2006-247978 filed in Japan Patent Office on Sep. 13 in 2006, the entire contents of which are hereby incorporated by reference.

What is claimed is:

1. An examination container comprising:
a container; and
an examination element provided in the container, the examination element comprising:
a battery;
an antenna configured to receive a wireless signal transmitted from an external device;
a rectifying circuit converting the wireless signal received by the antenna into direct current;
a charge circuit configured to generate current based on an electric power from the rectifying circuit and charge the battery, the charge circuit comprising a constant current source and a switch circuit;
a charge control circuit configured to monitor an amount of charge in the battery;
a reagent portion configured to be in contact with a liquid;
a sensor configured to detect a change of color or a colored degree of the reagent portion;
an insulating layer covering the sensor, wherein the reagent portion is provided over the insulating layer; and
a semiconductor device capable of wireless communication,
wherein the battery is connected to the sensor, the semiconductor device, the charge circuit, and the charge control circuit,
wherein the semiconductor device comprises a memory circuit and a circuit,
wherein the circuit is configured to perform an analytical processing of data of the change of color or the colored degree of the reagent portion detected by the sensor,
wherein the memory circuit is configured to store data processed by the circuit,
wherein the semiconductor device is configured to transmit the data processed by the circuit and stored in the memory circuit to an external database,
wherein a first terminal of the switch circuit is electrically connected to the constant current source,
wherein a second terminal of the switch circuit is electrically connected to the battery,
wherein the charge control circuit is configured to output low-level potential to a third terminal of the switch circuit so that the first terminal of the switch circuit is electrically connected to the second terminal of the switch circuit when the battery is not overcharged, and
wherein the charge control circuit is configured to output high-level potential to the third terminal of the switch circuit so that the first terminal of the switch circuit is not electrically connected to the second terminal of the switch circuit when the battery is overcharged,
wherein the container is a cylindrical body with a bottom, and
wherein the examination element is attached to the bottom.

2. The examination container according to claim 1, wherein the sensor comprises a photo diode and an amplifier circuit configured to amplify an output current of the photo diode.

3. The examination container according to claim 1, further comprising a hygroscopic portion in contact with the reagent portion.

4. The examination container according to claim 1, wherein the examination element is used for urinalysis.

5. The examination container according to claim 1, wherein the reagent portion, the sensor and the semiconductor device are formed over a resin substrate.

6. The examination container according to claim 1, wherein the container is a paper cup.

7. The examination container according to claim 1, wherein data of a serial number for examination or personal information is stored in the memory circuit in advance.

8. The examination container according to claim 1,
wherein the battery is a thin-film secondary battery with a thickness of 10 μm or less.

9. An examination container comprising:
a container; and
an examination element provided in the container,
the examination element comprising:
- a battery;
- an antenna configured to receive a wireless signal transmitted from an external device;
- a rectifying circuit converting the wireless signal received by the antenna into direct current;
- a charge circuit configured to generate current based on an electric power from the rectifying circuit and charge the battery, the charge circuit comprising a constant current source and a switch circuit;
- a charge control circuit configured to monitor an amount of charge in the battery;
- a reagent portion configured to be in contact with a liquid;
- a light source configured to irradiate the reagent portion with light;
- a sensor configured to detect a change of color or a colored degree of the reagent portion; and
- a semiconductor device capable of wireless communication, wherein the battery is connected to the sensor, the semiconductor device, the charge circuit, and the charge control circuit,
wherein the semiconductor device comprises a memory circuit and a circuit,
wherein the circuit is configured to perform an analytical processing of data of the change of color or the colored degree of the reagent portion detected by the sensor,
wherein the memory circuit is configured to store data processed by the circuit,
wherein the semiconductor device is configured to transmit the data processed by the circuit and stored in the memory circuit to an external database,
wherein the sensor comprises a thin film transistor formed over a substrate,
wherein the light source is a light emitting diode,
wherein a first terminal of the switch circuit is electrically connected to the constant current source,
wherein a second terminal of the switch circuit is electrically connected to the battery,
wherein the charge control circuit is configured to output low-level potential to a third terminal of the switch circuit so that the first terminal of the switch circuit is electrically connected to the second terminal of the switch circuit when the battery is not overcharged,
wherein the charge control circuit is configured to output high-level potential to the third terminal of the switch circuit so that the first terminal of the switch circuit is not electrically connected to the second terminal of the switch circuit when the battery is overcharged, and
wherein the reagent portion, the light source, the sensor, and the semiconductor device are stacked with each other,
wherein the container is a cylindrical body with a bottom, and
wherein the examination element is attached to the bottom.

10. The examination container according to claim 9, wherein the sensor comprises a photo diode and an amplifier circuit configured to amplify an output current of the photo diode.

11. The examination container according to claim 9, further comprising a hygroscopic portion in contact with the reagent portion.

12. The examination container according to claim 9, wherein the examination element is used for urinalysis.

13. The examination container according to claim 9, wherein the reagent portion, the sensor and the semiconductor device are formed over a resin substrate.

14. The examination container according to claim 9, wherein the container is a paper cup.

15. The examination container according to claim 9,
wherein data of a serial number for examination or personal information is stored in the memory circuit in advance.

16. The examination container according to claim 9,
wherein the battery is a thin-film secondary battery with a thickness of 10 μm or less.

* * * * *